US012799542B2

(12) United States Patent
Medin et al.

(10) Patent No.: US 12,799,542 B2
(45) Date of Patent: Nov. 17, 2026

(54) SYSTEM AND METHOD FOR DETECTING AND MONITORING PATHOGENS

(71) Applicant: SNAPDNA

(72) Inventors: David Medin, Los Altos, CA (US); Veronica De Guzman, Palo Alto, CA (US); Zil Panchal, Fremont, CA (US)

(73) Assignee: SNAPDNA

( * ) Notice: Subject to any disclaimer, the term of this patent is extended or adjusted under 35 U.S.C. 154(b) by 1150 days.

(21) Appl. No.: 18/044,377

(22) PCT Filed: Jul. 22, 2020

(86) PCT No.: PCT/US2020/043112
§ 371 (c)(1),
(2) Date: Mar. 8, 2023

(87) PCT Pub. No.: WO2021/016374
PCT Pub. Date: Jan. 28, 2021

(65) Prior Publication Data

US 2024/0093313 A1 Mar. 21, 2024

Related U.S. Application Data

(60) Provisional application No. 62/877,783, filed on Jul. 23, 2019.

(51) Int. Cl.

| | |
|---|---|
| ***C12Q 1/689*** | (2018.01) |
| ***B01D 15/38*** | (2006.01) |
| ***B01L 3/00*** | (2006.01) |
| ***C12Q 1/6804*** | (2018.01) |
| ***C12Q 1/6851*** | (2018.01) |

(52) U.S. Cl.
CPC ......... *C12Q 1/689* (2013.01); *B01D 15/3809* (2013.01); *B01L 3/502761* (2013.01); *C12Q 1/6804* (2013.01); *B01L 2200/0652* (2013.01); *B01L 2200/16* (2013.01); *B01L 2300/0654* (2013.01); *B01L 2400/082* (2013.01); *C12Q 1/6851* (2013.01)

(58) Field of Classification Search
CPC .... C12Q 1/689; C12Q 1/6804; C12Q 1/6851; C12Q 1/04; C12Q 1/18; C12Q 1/24; B01D 15/3809; B01D 15/3804; B01L 3/502761; B01L 2200/0652; B01L 2200/16; B01L 2300/0654; B01L 2400/082; G01N 33/5308; G01N 33/569; G01N 33/56905; G01N 33/56911; G01N 33/56961; G01N 33/56983; G01N 2469/10
See application file for complete search history.

(56) References Cited

U.S. PATENT DOCUMENTS

2014/0227723 A1 * 8/2014 Ingber ..................... A61P 31/04 530/387.3
2016/0250638 A1 9/2016 Havard

FOREIGN PATENT DOCUMENTS

CA 2895945 A1 * 6/2014 ............... C12Q 1/24

OTHER PUBLICATIONS

Internatioanl Search Report and Writen Opinion of PCT/US2020/043112, Mailed Dec. 18, 2020.

* cited by examiner

*Primary Examiner* — Cynthia B Wilder
(74) *Attorney, Agent, or Firm* — NEXUS IP LAW PLLC

(57) ABSTRACT

Disclosed herein are systems, methods and kits for detecting and monitoring pathogens, such as bacterial, fungal and viral foodborne pathogens.

51 Claims, 11 Drawing Sheets

FIG. 4

| | Sample | Tested strain | | Source | Positive Signal |
|---|---|---|---|---|---|
| Gram-positive bacteria | *Listeria monocytogenes* | RM2199 | | Human | YES |
| | *Bacillus cereus* | ATCC 14579 | | Soil | NO |
| | | RM5142 (6A2) | | Soil | |
| | | RM5143 (6A3) | | Soil | |
| | *Bacillus subtilis* subsp. *spizizenii* | ATCC 6633 | | Soil | |
| Gram-negative bacteria | *Citrobacter freundii* | RM4680 | | Lettuce | |
| | *Enterobacter cloacae* | RM9194 | | Spinach | |
| | *Pseudomonas syringae* | RM1952 (B728a) | | Bean | |
| | Negative Control | Not applicable | | Not applicable | |

SYSTEM AND METHOD FOR DETECTING AND MONITORING PATHOGENS

CROSS REFERENCE TO RELATED APPLICATION

This application is a continuation of International Patent Application No. PCT/US2020/043112 with a filing date of Jul. 22, 2020, designating the United States, now pending, and further claims priority to U.S. provisional application 62/877,783 with a filing date of Jul. 23, 2019. The content of the aforementioned applications, including any intervening amendments thereto, are incorporated herein by reference.

FIELD

This disclosure relates to the field of pathogens and in particular, to systems and methods for detecting and monitoring pathogens, such as bacterial, fungal and viral foodborne pathogens.

BACKGROUND

Bacterial and viral foodborne pathogens are responsible for a consistent level of human illness that poses a substantial public health and economic burden. Approximately one in six Americans contracts a foodborne illness each year with an estimated annual economic impact of approximately $16billion. A primary obstacle to rapid food pathogen analysis today is having a method that is sensitive enough to capture and detect a pathogen. Therefore, current methodologies rely on enrichment for obtaining enough cell numbers for detection of bacterial fungal, and some viral pathogens. Depending on which pathogen is targeted for detection and the effectiveness of the enrichment media this step can take from 8 hours to 24 hours or longer for incubation times. Further, since culturing is not yet feasible for all foodborne pathogens, standard culture-based methods cannot analyze samples for some enteric viral pathogens. Therefore, improved assays and methods for detecting and monitoring foodborne pathogens are needed.

SUMMARY

Some of the primary drivers for culturing in foodborne pathogen detection and analysis include the need for high copy count to meet the detection assay limit of detection (LOD) and to dilute assay inhibitors in the original sample. The "holy grail" of foodborne pathogen detection is a field-deployable or on-site instrument with disposable, single-use cartridges for rapid, culture-independent sample preparation, and bacterial, fungal and viral pathogen analysis for use in surveillance and attribution by regulatory and public health agencies, food industry, and other researchers. The system ideally isolates and analyzes live cells, detects 1 colony forming unit (CFU) per 25 mL, processes large and complex sample matrices, and provides semi-quantitative, sample-to-answer results in a short amount of time, such as 90 minutes or less.

Disclosed herein are systems and methods which eliminate the need to culture bacteria or fungi and delivers all the industry required and delivered capabilities for foodborne pathogen detection. The disclosed assays and methods provide a culture-independent analysis of environmental, food and water samples to enable a rapid, portable, highly sensitive and specific detection of pathogens at the point of need. Eliminating the need for culturing prior to analysis greatly reduces total-time-to-results for pathogen testing, enables quantitative analysis, and enables effective intervention strategies to reduce and mitigate the presence of pathogens in the food supply. It also dramatically reduces the time needed to systematically identify, isolate, eradicate, and confirm remediation and resolution of pathogen contamination. This can greatly reduce the number of people sickened and the overall economic impact from pathogens in the food supply. The food industry typically holds finished product in storage for three days or more while waiting for pathogen test results. For food processors, the disclosed assay and method will reduce the operational costs associated with storing food and will facilitate a much more flexible and customer-driven food supply chain model, significantly reducing the time required to react to an order, the quantity of inventory needed to be carried, and the amount of waste due to spoilage.

In some embodiments, a disclosed system and method uses aptamer-based pathogen capture or antibody/antigen pathogen capture followed by releasing pathogens from aptamers or antibodies. For example, an assay uses DNA aptamers to specifically sequester pathogens away from the contaminating matrix, including other non-targeted organisms and nucleic acid amplification inhibitors, all of which can be removed through aggressive and thorough washing prior to DNA/RNA extraction, amplification, and analysis.

In some embodiments, a method for detecting, quantitating and/or monitoring pathogens, comprises:

capturing one or more live pathogens from a contaminating matrix within a sample by aptamer-based capture or antibody-based capture; and releasing the one or more captured live pathogens from aptamers or antibodies, thereby allowing the one or more live pathogens to be detected, quantitated and/or monitored without requiring cell culture.

In some embodiments, the one or more live pathogens is one or more disease producing organism, such as bacteria, fungi, protozoa and/or worms.

In some embodiments, the one or more live pathogens is one or more pathogens in a sample from food, water, environment, soil, plant, animal, insect, or human.

In some embodiments, capturing one or more live pathogens comprises applying the sample to a pathogen-isolation column containing multiple beads of one or more sizes.

In some embodiments, cross-sectional area of the pathogen capture column is constant.

In some embodiments, cross-sectional area of the pathogen capture column varies.

In some embodiments, cross-section of the pathogen capture column is of a uniform shape, such as of a circle, oval or polygon.

In some embodiments, cross-section of the pathogen capture is a non-uniform shape.

In some embodiments, magnesium is present at pathogen capture at a concentration sufficient to increase aptamer melting temperatures to result in stable secondary structure formation while in the presence of less than 100 mM sodium and less than 20 degrees Celsius.

In some embodiments, the magnesium concentration is more than 0.1 mM.

In some embodiments, bead surface of each of the multiple beads comprises of a material that has been modified for aptamer or antibody attachment.

In some embodiments, capturing one or more live pathogens further comprises applying the sample to a pre-filter container containing beads of same size or smaller than pathogen-isolation column prior to the pathogen-isolation column containing multiple beads of one or more sizes.

In some embodiments, the beads of the pre-filter container have non-fouling surface properties.

In some embodiments, capturing one or more live captured pathogens from aptamers or antibodies, comprises: optional conditioning of the pre-filter container and capture column by flowing liquid through the pre-filter container and capture column.

In some embodiments, the sample is a pathogen sample.

In some embodiments, the method further comprises washing the one or more live captured pathogens prior to releasing the live captured one or more pathogens to remove substances not specifically bound.

In some embodiments, substances not specifically bound comprise non-targeted organisms and nucleic acid amplification inhibitors.

In some embodiments, releasing the one or more live captured pathogens from aptamers or antibodies, comprises washing the captured one or more live pathogens with a release buffer.

In some embodiments, releasing the one or more captured live pathogens from aptamers or antibodies is performed by using a flow rate equal to or higher than the flow rate used to capture the one or more pathogens.

In some embodiments, the flow rate for releasing the one or more captured live pathogens from aptamers or antibodies is at least 2× higher than the flow rate for capturing the one or more pathogens.

In some embodiments, releasing the one or more live captured pathogens from aptamers or antibodies, comprises an air gap prior to washing the captured one or more live pathogens with a release buffer.

In some embodiments, the released live pathogens are optionally collected in liquid in a vented bubble trap acting as a reservoir and acting to remove air prior to the one or more live pathogens in liquid are flowed through a filter to collect the released one or more pathogens.

In some embodiments, the vented bubble trap comprises at least one inlet port, at least one outlet port, and a vent to air.

In some embodiments, the vent optionally comprises one or more sensors that permit feedback control of volume of liquid pumped into the vented bubble trap.

In some embodiments, the one or more sensors comprise one or more liquid level sensors capable of detecting liquid level and/or one or more bubble sensors capable of detecting bubbles in the liquid.

In some embodiments, the method is aptamer-based and aptamers are used to specifically sequester pathogens away from the contaminating matrix.

In some embodiments, the aptamer contains DNA, RNA, PNA, peptide or other natural or synthetic molecules In some embodiments, the method further comprises detecting, quantitating and/or monitoring pathogens by performing nucleic acid detection following releasing captured live pathogens.

In some embodiments, nucleic acid detection comprises detecting DNA or RNA.

In some embodiments, nucleic acid detection comprises performing polymerase chain reaction, isothermal amplification, hybridization detection, and/or sequencing.

In some embodiments, one or more steps of the disclosed method is performed by automation.

In some embodiments, the method further comprises sanitizing after performing the method of detecting, detecting, quantitating and/or monitoring pathogens.

In some embodiments, sanitizing comprises employing a sanitation system comprising a cartridge and a sanitation solution for sanitation prior to or following use of system for detecting, monitoring or quantitating one or more pathogens.

In some embodiments, the method further comprises applying a sample temperature by one or more cooling or heating elements to transfer the temperature to the sample prior to pathogen capture.

In some embodiments, a system for detecting, quantitating and/or monitoring pathogens, comprises: a sample input source for holding the sample prior to processing; a sample straw coupled to the sample input source; a pump coupled to the sample straw for providing the sample for processing; and one or more sensors to detect when sufficient sample volume is collected or sample volume is no longer detectable.

In some embodiments, the one or more sensors comprises one or more liquid level sensors capable of detecting liquid level and/or one or more bubble sensors capable of detecting bubbles in the liquid.

In some embodiments, the system further comprises a process for notifying an insufficient sample volume being acquired.

In some embodiments, the system further comprises a pathogen capture system coupled to the sample straw, wherein one or more pathogens are captured and a method to analyze the captured pathogen.

In some embodiments, the sample input source is a temporary or permanent bag or reservoir.

In some embodiments, the straw is temporary or permanent.

In some embodiments, the system further comprises a sanitation system for sanitation prior to or following use of the system.

In some embodiments, the sanitation system comprises a sanitation cartridge and sanitation solution for sanitation prior to or following use of system for detecting, monitoring or quantitating one or more pathogens.

In some embodiments, a method for detecting, quantitating and/or monitoring pathogens, comprises: capturing one or more foodborne pathogens from a contaminating matrix within a sample by aptamer-based pathogen capture or antibody/antigen pathogen capture; and releasing the one or more captured foodborne pathogens from aptamers or antibodies, thereby allowing the one or more foodborne pathogens to be detected, quantitated and/or monitored without requiring cell culture.

In some embodiments, a method for capturing live pathogens from a contaminating sample matrix by aptamer-based pathogen capture, comprises: reducing sodium concentration to less than 100 mM in pathogen capturing conditions; reducing temperature to less than 20 degrees Celsius in pathogen capturing conditions; and providing magnesium at a concentration greater than 0.1 mM and sufficient to increase aptamer melting temperatures to result in a stable secondary structure formation.

In some embodiments, the method further comprises applying a sample temperature by one or more cooling or heating elements to transfer the sample temperature to the sample prior to pathogen capture.

In some embodiments, a method for capturing live pathogens from a contaminating sample matrix by aptamer-based pathogen capture, comprises: reducing sodium concentration to less than 70 mM in pathogen capturing conditions; reducing temperature to less than 20 degrees Celsius in pathogen capturing conditions; and providing magnesium at a concentration greater than 0.25 mM and sufficient to increase aptamer melting temperatures to result in desired secondary structure formation.

In some embodiments, the method further comprises applying a sample temperature by one or more cooling or heating elements to transfer the temperature to the sample prior to pathogen capture.

In some embodiments, a method for detecting, quantitating and/or monitoring infectious particles, comprises: capturing one or more infectious particles from a contaminating matrix within a sample by aptamer-based capture or antibody/antigen capture; and releasing the one or more captured infectious particles from aptamers or antibodies, thereby allowing the one or more infectious particles to be detected, quantitated and/or monitored without requiring cell culture.

In some embodiments, the one or more infectious particles is one of bacteria, viruses, fungi, protozoa, worms, proteins and peptides.

In some embodiments, capturing one or more infectious particles comprises applying the sample to an isolation column containing multiple beads of one or more sizes.

In some embodiments, bead surface of each of the multiple beads comprises a material that has been modified for aptamer or antibody attachment.

In some embodiments, capturing one or more infectious particles further comprises applying the sample to a pre-filter container containing beads of same size or smaller than isolation column prior to the isolation column containing multiple beads of one or more sizes.

In some embodiments, the beads of the pre-filter container have non-fouling surface properties.

In some embodiments, the method further comprises washing the one or more captured infectious particles prior to releasing the one or more captured infectious particles.

In some embodiments, the one or more released captured infectious particles from aptamers or antibodies are concentrated prior to detection.

In some embodiments, the aptamer contains DNA, RNA, PNA, peptides or other natural or synthetic molecules.

In some embodiments, the method further comprises nucleic acid extraction prior to detection.

In some embodiments, detection contains nucleic acid detection comprising detecting DNA or RNA.

In some embodiments, nucleic acid detection comprises performing polymerase chain reaction, isothermal amplification, hybridization detection, and/or sequencing.

In some embodiments, a system to automatically link a machine-readable code on a sample collection bag from a food industry sample to sample analysis results, comprises: a machine-readable code on the sample collection bag; a machine-readable code on a bag used for paddle blending a sample; a machine-readable code on a cartridge used for sample analysis; a method to determine sample analysis results; and a database to automatically link the machine-readable code on the sample collection bag to the sample analysis.

In some embodiments, the sample collection bag and the bag used for paddle blending the sample are the same bag.

In some embodiments, the machine-readable code on the cartridge optionally links to a type of analysis for that cartridge.

In some embodiments, the database to link the machine-readable code on the sample collection bag resides on a server accessible from a computer network.

In some embodiments, sample collection information is linked to the machine-readable code on a cartridge.

In some embodiments, sample collection information is linked to the machine-readable code on the cartridge to confirm the cartridge is capable of performing an analysis, comprises: determining type of pathogens or infectious agents the cartridge has been configured to analyze; and determining viability of the cartridge, such as the age and whether the cartridge has been previously used.

In some embodiments, the food industry sample is one or more of a food product or a food processing environmental sample.

In some embodiments, the food industry sample is paddle blending with more than 25 milliliters of an aqueous solution prior to analysis.

In some embodiments, a method for detecting, quantitating and/or monitoring pathogens, comprises: applying a contaminating matrix to a removable cartridge containing non-volatile digital data; the capability to write digital data when the cartridge is manufactured; and the capability to read and write cartridge digital data prior to, during and following sample analysis.

In some embodiments, the pathogen is one of bacteria, viruses, fungi, protozoa, worms, proteins and peptides from one or more of food, water, environment, soil, plant, animal, insect, or human.

In some embodiments, the digital data can be associated with one of cartridge manufacturing information, cartridge storage information, cartridge viability, cartridge lifetime, one or more pathogens the cartridge is designed for, the type of sample to be applied to the cartridge, data related to cartridge prior uses, and cartridge use data.

In some embodiments, the cartridge digital data can be automatically written one or more of prior to analysis, during analysis or following analysis.

In some embodiments, a system for generating a graphical representation of analysis data, comprises a coordinate axis wherein a first and second axis of each data point can be correlated to sample collection location and number of pathogens at each location is represented by one or more of a third coordinate axis, values and one or more differences in color, hue or intensity.

In some embodiments, sample collection location is one or more locations where samples are collected, such as where food is processed, prepared, distributed and/or sold or a location where people are present, such as changing rooms, or one or more locations of a farm, field or slaughterhouse.

The foregoing and other features of the disclosure will become more apparent from the following detailed description, which proceeds with reference to the accompanying figures.

BRIEF DESCRIPTION OF THE DRAWINGS

FIGS. 3 and 4 illustrate the specificity of an exemplary embodiment of a probe-based assay for target RNA detection in the presence of excess non-target RNA. The specificity of the probe-based assay for detecting 100 fg of *Listeria* RNA was tested using 20 ng of non-target RNA, which was equivalent to approximately 2 million non-target cells and 4 billion copies of non-target RNA sequences. The non-target RNA was extracted from environmental gram-positive bacterial strains, *Bacillus cereus* and *Bacillus subtilis* subsp. *spizenzeii*, which are closely related to *L. monocytogenes* as well as gram-negative bacterial strains, *Citrobacter freundii, Enterobacter cloacae*, and *Pseudomonas syringae*. No amplification (no Ct-value recorded) was detected in all of the non-target strains tested when using the probe-based assay.

DETAILED DESCRIPTION OF SEVERAL EMBODIMENTS

I. Terms

Figure 1:
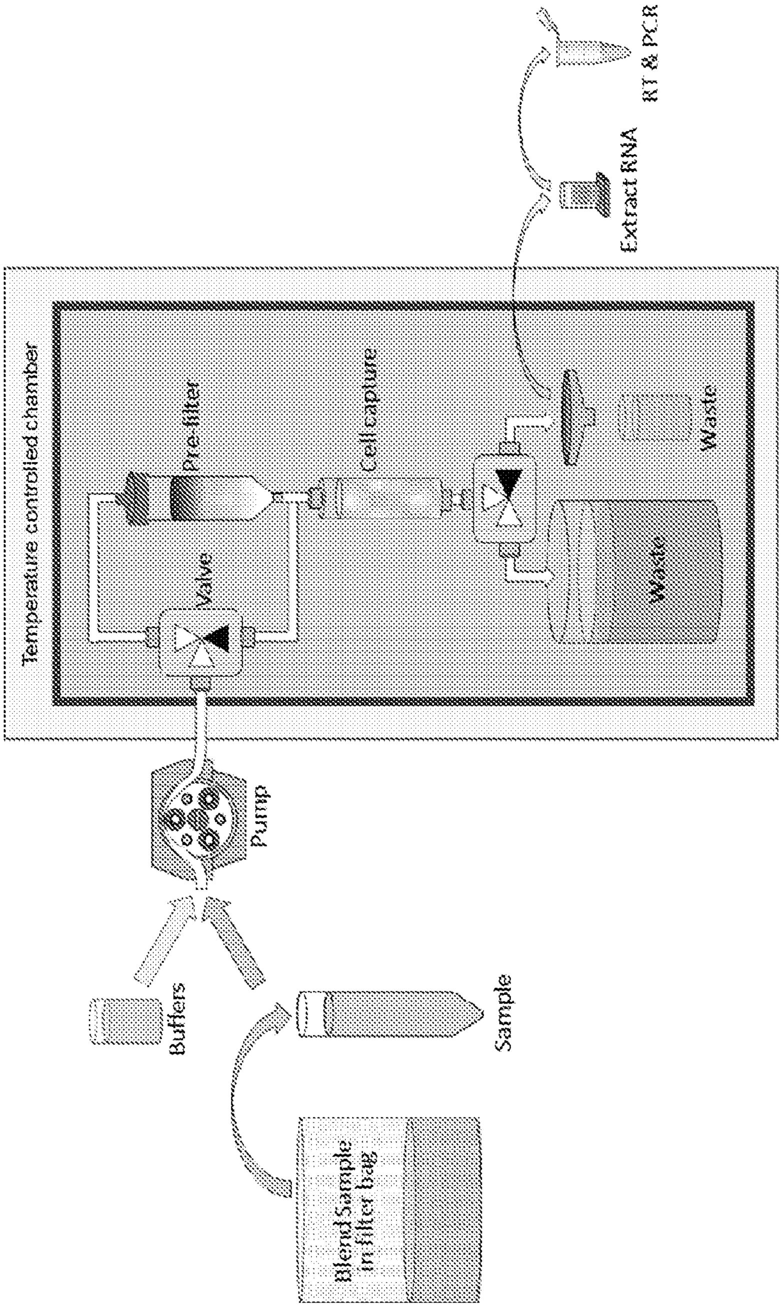
FIG. 1 is a schematic diagram of sample processing steps in accordance with an exemplary embodiment.
Figure 2:
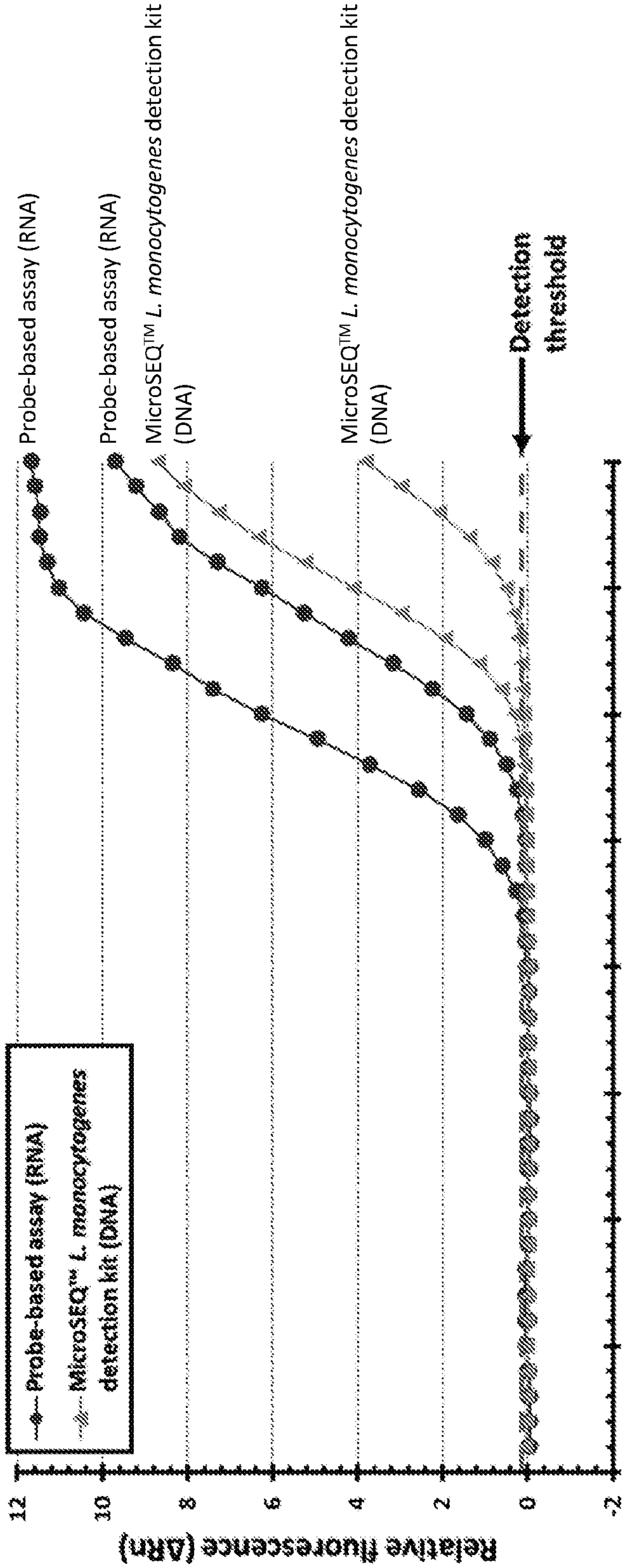
FIG. 2 is a graph illustrating improved sensitivity of an exemplary embodiment of the disclosed probe-based assay when compared to commercial kit widely used by the food industry. The performance of the disclosed probe-based assay was compared with a commercial kit, MicroSEQ™ *Listeria monocytogenes* Detection kit. A cell lysate of *L. monocytogenes* and 10 fold dilution of the lysate was split and were tested with the probe-based assay and the MicroSEQ™ assay. The disclosed probe-based assay was found to be 1000-times more sensitive than the commercial kit.
Figure 3:
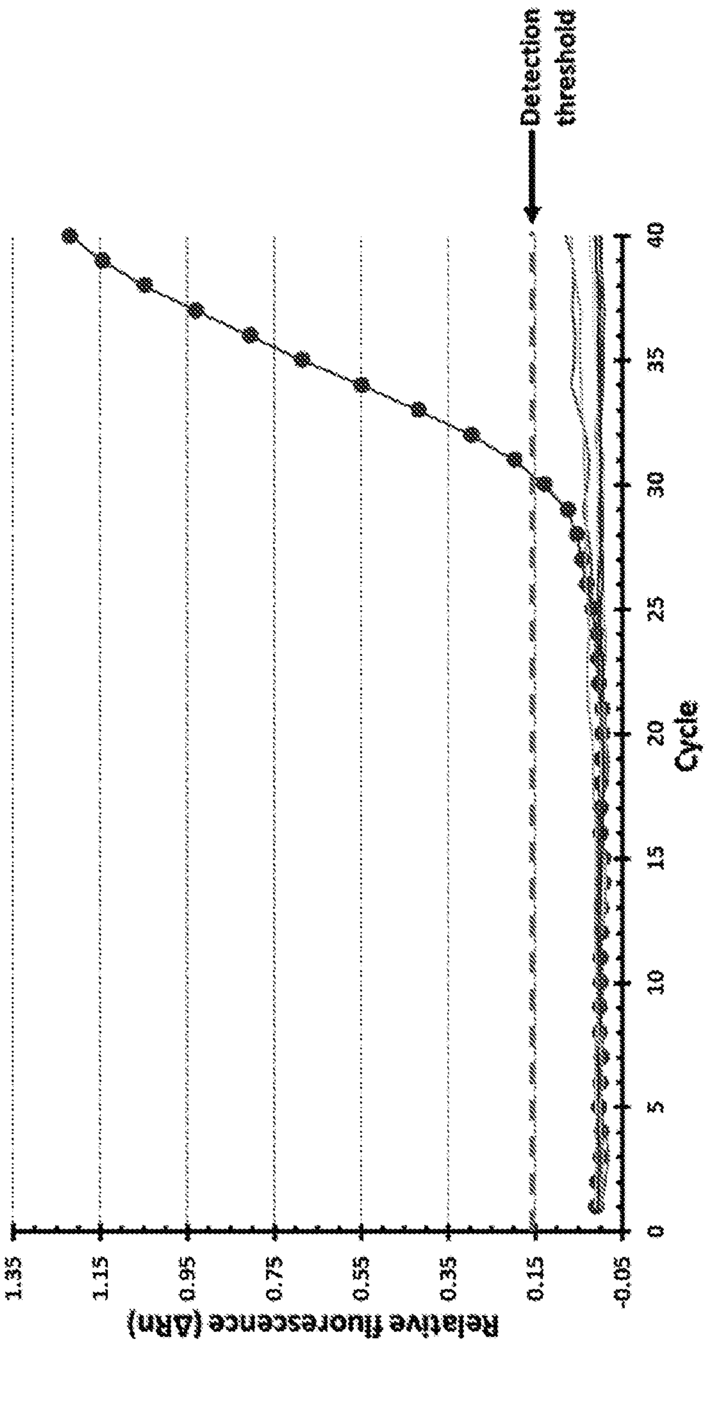
Figure 5:
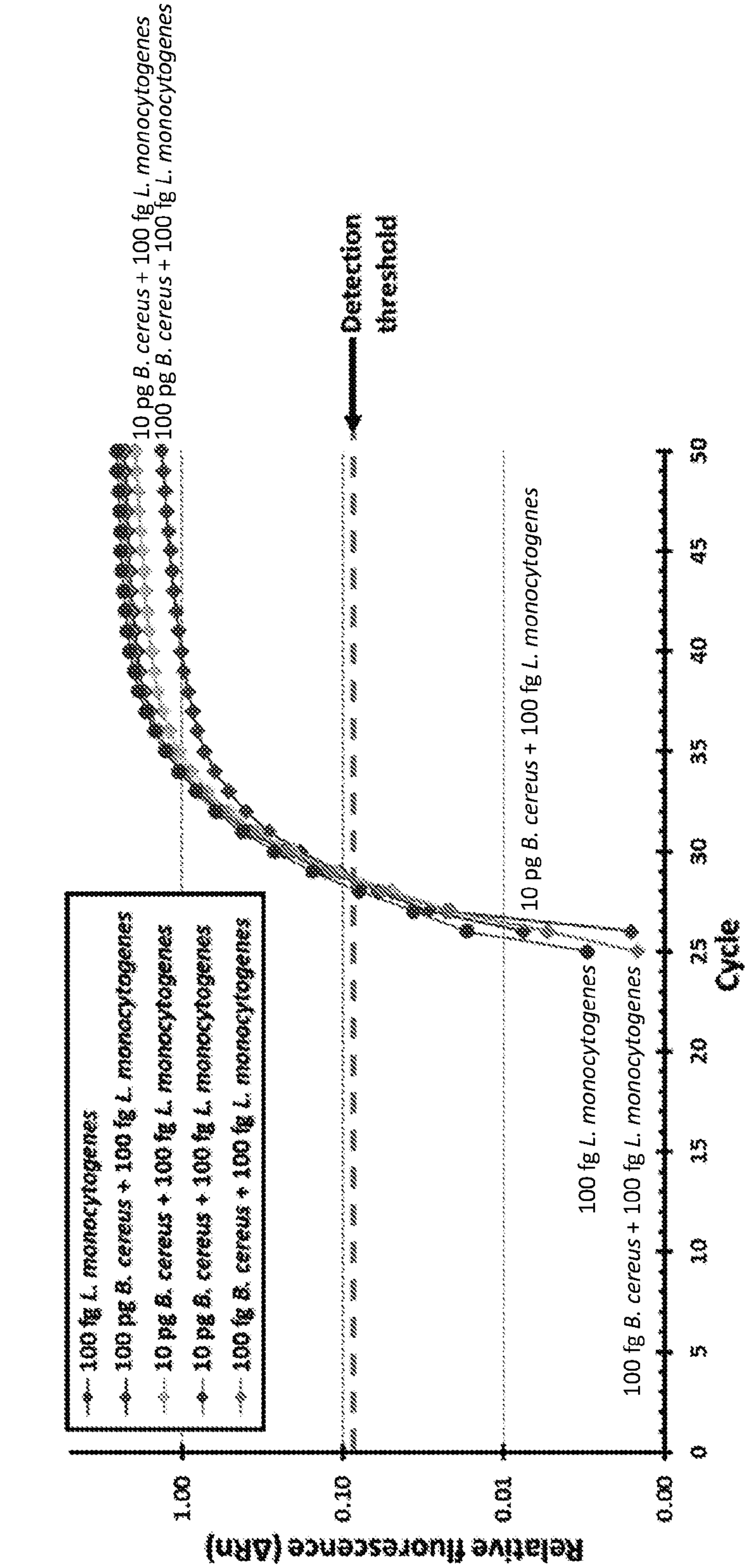
FIG. 5 is a graph illustrating co-incubation of purified target nucleic acid from *L. monocytogenes* vs excess non-target nucleic acid from *B. cereus*. Assay sensitivity was not affected in the presence of excess non target. To further validate the specificity of the probe-based assay by co-incubating low amounts of RNA from *Listeria monocytogenes* in the presence of various amounts of *Bacillus cereus* strain ATCC 14579. Results indicated that no significant differences in the Ct-values were observed. To examine the effect of various amounts of *Bacillus* RNA on the efficiency of the amplification of the *Listeria* sequences, the slope of the curve at the pre-inflection point was examined. Analysis of the amplification curve resulted in no significant change in the slope of the curve under the various conditions tested, demonstrating that the efficiency of the amplification may not be adversely affected by addition of the non-target template.
Figure 6:
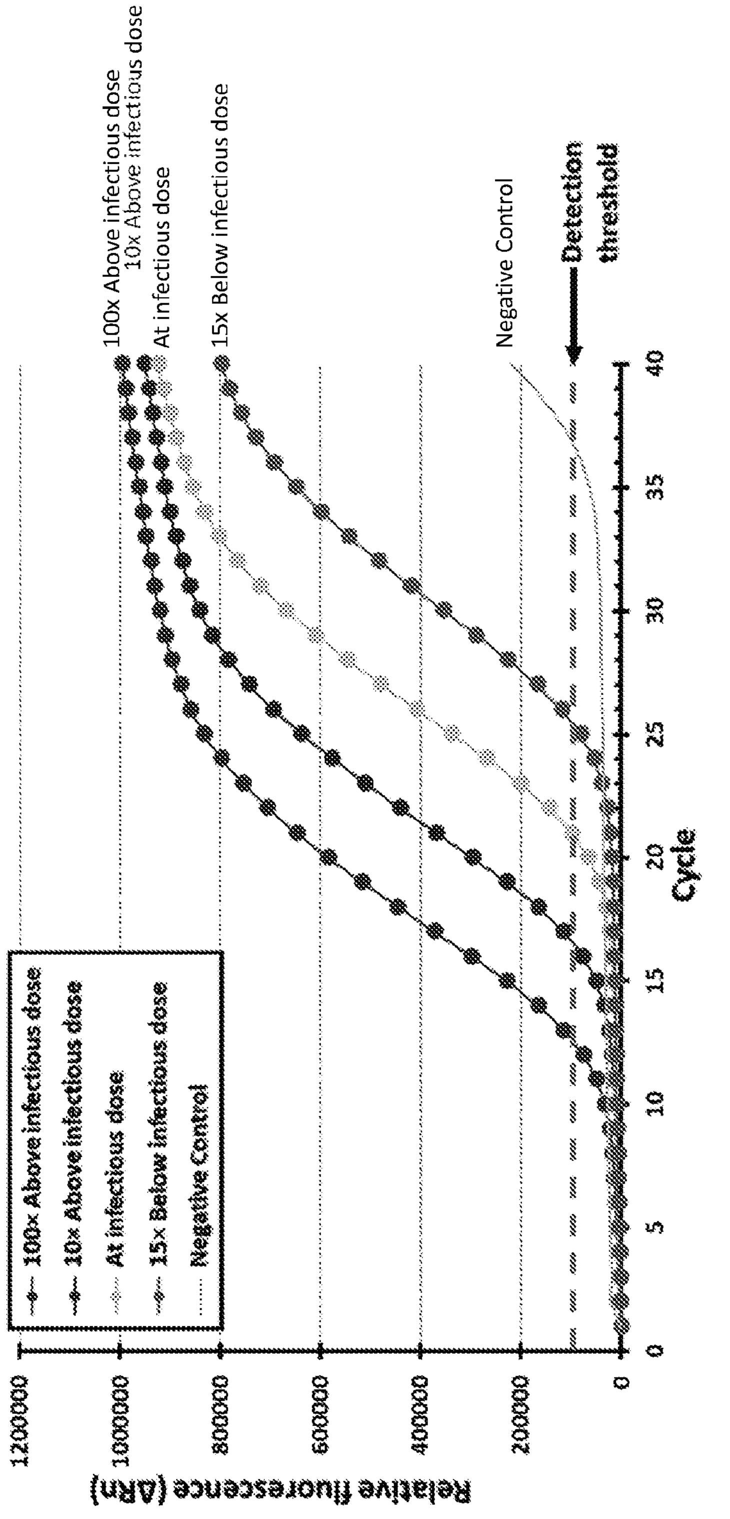
FIG. 6 is a graph illustrating sensitivity analysis with a disclosed platform. Assay was sensitive with close to 100% efficiency. Sensitivity was tested with reactions containing over an estimated 1,000,000 cells of *L. grayi* determined by measuring optical density and 16-fold serial dilutions of the samples to less than an estimated infectious dose of 1000 cells. The Ct-values of the serial dilutions were about 4 cycles apart indicating close to 100% efficiency.
Figure 7:
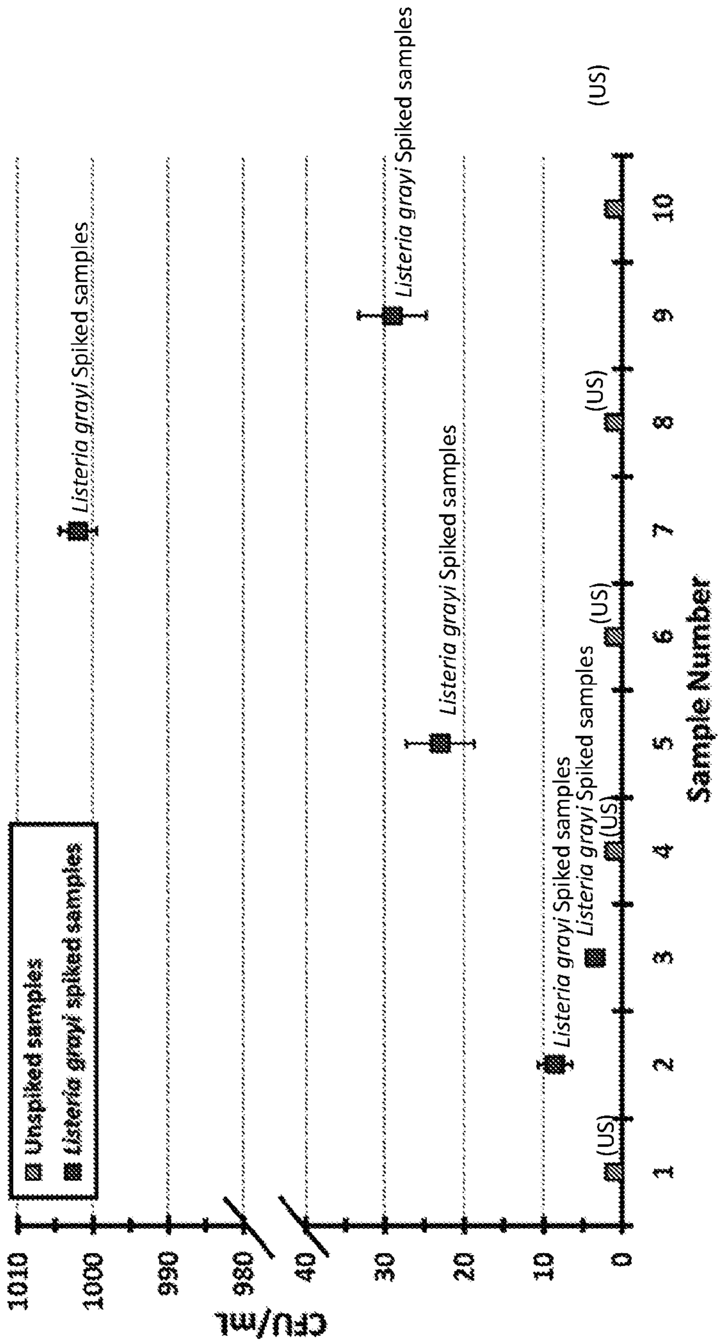
FIG. 7 is a graph illustrating swab sample enumeration results (blind study). Ten environmental samples selected to be as representative and challenging as possible were obtained collected from fresh produce facilities using stick-mounted sponges such as the 3M Sponge-Stick, typically pre-wetted with 10 mL of neutralizing buffer. After collection, 90 mL of buffer is added to a filter bag and the sponge is processed in a paddle blender, such as the Seward Stomacher, for 2 minutes to release the pathogen cells into the buffer. Five of the environmental samples were spiked with *Listeria grayi* in a blinded fashion, and 1 mL aliquots were withdrawn from each sample tube and plate enumerated. As shown by the enumeration results in the figure the *Listeria grayi* concentration were detected in the samples ranged from 3.5 CFU/mL and up. The disclosed DNA-based platform demonstrated the ability to process "real-world" environmental sponge samples and to accurately identify those samples spiked with *Listeria* and those which were unspiked.

The following explanations of terms and methods are provided to better describe the present disclosure and to guide those of ordinary skill in the art in the practice of the present disclosure. Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the scope of the disclosure.

The terms "coupled" and "connected," along with their derivatives, may be used. These terms are not intended as synonyms for each other. Rather, aspects, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but still cooperate or interact with each other.

For the purposes of the description, a phrase in the form "A/B" or in the form "A and/or B" means)A(,)B(,or)A and B. (For the purposes of the description, a phrase in the form "at least one of A, B, and C" means (A), (B), (C), (A and B), (A and C), (B and C), or)A, B and C(. For the purposes of the description, a phrase in the form")A(B" means)B (or)AB (that is, A is an optional element.

The singular terms "a," "an," and "the" include plural referents unless context clearly indicates otherwise. Similarly, the word "or" is intended to include "and" unless the context clearly indicates otherwise. The term "comprises" means "includes." Thus, "comprising A or B," means "including A, B, or A and B," without excluding additional elements.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms) e.g., the term "including" should be interpreted as "including but not limited to," the term "having" should be interpreted as "having at least," the term "includes" should be interpreted as "includes but is not limited to," etc. (.

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Unless otherwise noted, technical terms are used according to conventional usage. Definitions of common terms in molecular biology can be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710); and other similar references.

Suitable methods and materials for the practice or testing of this disclosure are described below. Such methods and materials are illustrative only and are not intended to be limiting. Other methods and materials similar or equivalent to those described herein can be used. In addition, the materials, methods, and examples are illustrative only and not intended to be limiting.

All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various embodiments of this disclosure, the following explanations of specific terms are provided:

3' end: The end of a nucleic acid molecule that does not have a nucleotide bound to it 3' of the terminal residue.

5' end: The end of a nucleic acid sequence where the 5' position of the terminal residue is not bound by a nucleotide.

Agent: Any protein, nucleic acid molecule (including chemically modified nucleic acids), compound, antibody, small molecule, organic compound, inorganic compound, or other molecule of interest. Agent can include a therapeutic agent, a diagnostic agent or a pharmaceutical agent.

Amplification: A technique that increases the number of copies of a nucleic acid molecule) such as an RNA or DNA(. An example of amplification is polymerase chain reaction (PCR), in which a sample is contacted with a pair of oligonucleotide primers under conditions that allow for the hybridization of the primers to a nucleic acid template in the sample. The primers are extended under suitable conditions) e.g., in the presence of a polymerase enzyme and dNTPs(, dissociated from the template, re-annealed, extended, and dissociated to amplify the number of copies of the nucleic acid. The product of amplification can be characterized or quantified by electrophoresis, restriction endonuclease cleavage patterns, oligonucleotide hybridization or ligation, and/or nucleic acid sequencing using standard techniques. For example, the quantity and efficiency of the reaction can be determined using labels (as defined below), such as fluorescent reporters (including quenching reporters) in the amplification process. It can also be done without labels using methods such as UV spectroscopy. Various commercial products are also available, such as Qubit from ThermoFisher Scientific.

Other examples of amplification include quantitative real-time polymerase chain reaction) qPCR(, strand displacement amplification, as disclosed in U.S. Pat. No. 5,744,311; transcription-free isothermal amplification, as disclosed in U.S. Pat. No. 6,033,881; repair chain reaction amplification, as disclosed in PCT publication WO90/01069; ligase chain reaction amplification, as disclosed in European patent publication EP-A-320,308; gap filling ligase chain reaction amplification, as disclosed in U.S. Pat. No. 5,427,930; and NASBA RNA transcription-free amplification, as disclosed in U.S. Pat. No. 6,025,134. Several embodiments include multiplex qPCR assays, which are useful for amplifying and detecting multiple nucleic acid sequences in a single reaction.

Antibody: A polypeptide including at least a light chain or heavy chain immunoglobulin variable region which specifically recognizes and binds an epitope of an antigen, such as a SCLC associated molecule or a fragment thereof. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. Antibodies of the present disclosure include those that are specific for a disclosed SCLC-associated molecule.

The term antibody includes intact immunoglobulins, as well the variants and portions thereof, such as Fab' fragments, $F(ab)'_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook,* 1994-1995 (Pierce Chemical Co., Rockford, IL); Kuby, J., *Immunology,* 3rd Ed., W.H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds RET will have a specific $V_H$ region and the $V_L$ region sequence, and thus specific CDR sequences. Antibodies with different specificities (such as different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "polyclonal antibody" is an antibody that is derived from different B-cell lines. Polyclonal antibodies are a mixture of immunoglobulin molecules secreted against a specific antigen, each recognizing a different epitope. These antibodies are produced by methods known to those of skill in the art, for instance, by injection of an antigen into a suitable mammal (such as a mouse, rabbit or goat) that induces the B-lymphocytes to produce IgG immunoglobulins specific for the antigen, which are then purified from the mammal's serum.

A "chimeric antibody" has framework residues from one species, such as human, and CDRs (which generally confer antigen binding) from another species, such as a murine antibody that specifically binds a SCLC-associated molecule.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one example, all the CDRs are from the donor immunoglobulin in a humanized immunoglobulin. Constant regions need not be present, but if they are, they are ly identical to human immunoglobulin constant regions, e.g., at least about 85-90%, such as about 95% or more identical. Hence, all parts of a humanized immunoglobulin, except possibly the CDRs, are substantially identical to corresponding parts of natural human immunoglobulin sequences. Humanized immunoglobulins can be constructed by means of genetic engineering (see for example, U.S. Pat. No. 5,585,089).

An "autoantibody" is an antibody produced by the immune system that is directed against one or more of the individual's own proteins.

Alteration or modulation in expression: An alteration in expression of a gene, gene product or modulator thereof. This phrase refers to a change or difference, such as an increase or decrease, in the level of the gene, gene product, or modulators thereof that is detectable in a biological sample relative to a control or a reference value known to be indicative of the level of the gene, gene product or modulator thereof in the absence of the pathogen. An "alteration" in expression includes an increase in expression (up-regulation) or a decrease in expression (down-regulation).

Aptamer: The term "aptamer", as referred to herein, should be understood to include synthetic antibodies, peptide aptamers, and nucleic acid aptamers, at least a portion of which is able to bind to another molecule. Nucleic acid aptamers are generally single-stranded nucleic acid molecules with complex secondary or tertiary structures (which as discussed later may include double-stranded portions or regions) that can specifically bind a target molecule with high affinity. The aptamers contemplated for use herein can be any suitable nucleic acid or equivalent thereof. In this regard, the aptamers can include, for example, DNA, RNA, a nucleic acid analogue (XNA) such as Peptide Nucleic Acid (PNA) or Locked Nucleic Acid (LNA), glycol nucleic acid (GNA) or threose nucleic acid (TNA) or DNA or RNA comprising one or more modified nucleotides, and the like. Methods of developing and using aptamers are known to those of skill in the art, for example, see Reverdatto et al., Current Topics in Medicinal Chemistry, Vol. 15, Issue 12, 2015, which is hereby incorporated by reference in its entirety. "Modified" nucleotides include, for example, nucleotides having chemical modifications to any of the phosphate backbone, sugar moiety or base moiety of the nucleotide, tritylated bases and unusual bases such as inosine. The use of modified nucleotides can also affect the binding characteristics of the aptamer to the nuclease, for example as described in Latham et al. (Nucl Acids Res 22(14): 2817-2822, 1994 which is hereby incorporated by reference in its entirety).

In some specific embodiments, RNA aptamers are used. Nucleic acid aptamers can be modified, for example to increase stability, in a number of ways including, for example: (i) Synthesis of aptamers using L-nucleotides (the mirror image of natural nucleotides) so that they cannot be degraded by naturally occurring nucleases; (ii) Incorporation of locked nucleic acid (LNA) and/or peptide nucleic acid (PNA) residues into the aptamer. LNAs and PNAs also increase stability of nucleic acid duplexes; (iii) Other chemical modifications of ribonucleotides, such as 2'-amino- and 2'-fluoro-pyrimidine nucleotides or 2'-O-methyl nucleotides; and/or (iv) Capping at the 3' end with a deoxythymidine to increase resistance to exonuclease degradation. Nucleic acid aptamers can be produced using methods disclosed herein and known in the art. For example, in-vitro selection methods (e.g., see Ellington and Szostak, Nature 346(6287): 818-22, 1990, which is hereby incorporated by reference in its entirety) and SELEX methods (e.g., see Tuerk and Gold, Science 249(4968): 505-510, 1990 which is hereby incorporated by reference in its entirety) can be used. Further details relating to the production and selection of aptamers may also be found in the review of Osborne and Ellington (Chem Rev 97(2): 349-370, 1997, which is hereby incorporated by reference in its entirety). In some embodiments, aptamers include a linker (see, for example, idtdna.com/site/Catalog/Modifications/Category/2 as provided on Jul. 23, 2019 which are hereby incorporated by reference in their entireties) to facilitate attachment to a solid surface and may contain one or more spacers.

Bacterial pathogen: A bacteria that causes infection or disease (pathogenic bacteria). Examples of pathogenic bacteria include without limitation any one or more of (or any combination of) *Acinetobacter baumanii, Actinobacillus* sp., *Actinomycetes, Actinomyces* sp. (such as *Actinomyces israelii* and *Actinomyces naeslundii*), *Aeromonas* sp. (such as *Aeromonas hylrophila, Aeromonas veronii* biovar *sobria* (*Aeromonas sobria*), and *Aeromonas caviae*), *Anaplasma phagocytophilum, Anaplasma marginale, Alcaligenes xylosoxidans, Acinetobacter baumanii, Actinobacillus actinomycetemcomitans, Bacillus* sp. (such as *Bacillus anthracis, Bacillus cereus, Bacillus subtilis, Bacillus thuringiensis*, and *Bacillus stearothermophilus*), *Bacteroides* sp. (such as *Bacteroides fragilis*), *Bartonella* sp. (such as *Bartonella bacilliformis* and *Bartonella henselae, Bifidobacterium* sp., *Bordetella* sp. (such as *Bordetella pertussis, Bordetella parapertussis*, and *Bordetella bronchiseptica*), *Borrelia* sp. (such as *Borrelia recurrentis*, and *Borrelia burgdorferi*), *Brucella* sp. (such as *Brucella abortus, Brucella canis, Brucella melintensis* and *Brucella suis*), *Burkholderia* sp. (such as *Burkholderia pseudomallei* and *Burkholderia cepacia*), *Campylobacter* sp. (such as *Campylobacter jejuni,*

*Campylobacter coli, Campylobacter lari* and *Campylobacter fetus*), *Capnocytophaga* sp., *Cardiobacterium hominis, Chlamydia trachomatis, Chlamydophila pneumoniae, Chlamydophila psittaci, Citrobacter* sp. *Coxiella burnetii, Corynebacterium* sp. (such as, *Corynebacterium diphtheriae, Corynebacterium jeikeum* and *Corynebacterium*), *Clostridium* sp. (such as *Clostridium perfringens, Clostridium difficile, Clostridium botulinum* and *Clostridium tetani*), *Eikenella corrodens, Enterobacter* sp. (such as *Enterobacter aerogenes, Enterobacter agglomerans, Enterobacter cloacae* and *Escherichia coli*, including opportunistic *Escherichia coli*, such as enterotoxigenic *E. coli*, enteroinvasive *E. coli*, enteropathogenic *E. coli*, enterohemorrhagic *E. coli*, enteroaggregative *E. coli* and uropathogenic *E. coli*) *Enterococcus* sp. (such as *Enterococcus faecalis* and *Enterococcus faecium*) *Ehrlichia* sp. (such as *Ehrlichia chafeensia* and *Ehrlichia canis*), Erysipelothrix rhusiopathiae, *Eubacterium* sp., *Francisella tularensis, Fusobacterium nucleatum, Gardnerella vaginalis, Gemella morbillorum, Haemophilus* sp. (such as *Haemophilus influenzae, Haemophilus ducreyi, Haemophilus aegyptius, Haemophilus parainfluenzae, Haemophilus haemolyticus* and *Haemophilus parahaemolyticus, Helicobacter* sp. (such as *Helicobacter pylori, Helicobacter cinaedi* and *Helicobacter fennelliae*), *Kingella kingii, Klebsiella* sp. (such as *Klebsiella pneumoniae, Klebsiella granulomatis* and *Klebsiella oxytoca*), *Lactobacillus* sp., *Listeria monocytogenes, Leptospira interrogans, Legionella pneumophila, Leptospira interrogans, Peptostreptococcus* sp., *Mannheimia hemolytica, Moraxella catarrhalis, Morganella* sp., *Mobiluncus* sp., *Micrococcus* sp., *Mycobacterium* sp. (such as *Mycobacterium leprae, Mycobacterium tuberculosis, Mycobacterium paratuberculosis, Mycobacterium intracellulare, Mycobacterium avium, Mycobacterium bovis*, and *Mycobacterium marinum*), *Mycoplasm* sp. (such as *Mycoplasma pneumoniae, Mycoplasma hominis*, and *Mycoplasma genitalium*), *Nocardia* sp. (such as *Nocardia asteroides, Nocardia cyriacigeorgica* and *Nocardia brasiliensis*), *Neisseria* sp. (such as *Neisseria gonorrhoeae* and *Neisseria meningitidis*), *Pasteurella multocida, Plesiomonas shigelloides. Prevotella* sp., *Porphyromonas* sp., *Prevotella melaninogenica, Proteus* sp. (such as *Proteus vulgaris* and *Proteus mirabilis*), *Providencia* sp. (such as *Providencia alcalifaciens, Providencia rettgeri* and *Providencia stuartii*), *Pseudomonas aeruginosa, Propionibacterium acnes, Rhodococcus equi, Rickettsia* sp. (such as *Rickettsia rickettsii, Rickettsia akari* and *Rickettsia prowazekii, Orientia tsutsugamushi* (formerly: *Rickettsia tsutsugamushi*) and *Rickettsia typhi*), *Rhodococcus* sp., *Serratia marcescens, Stenotrophomonas maltophilia, Salmonella* sp. (such as *Salmonella enterica, Salmonella typhi, Salmonella paratyphi, Salmonella enteritidis, Salmonella cholerasuis* and *Salmonella typhimurium*), *Serratia* sp. (such as *Serratia marcesans* and *Serratia liquifaciens*), *Shigella* sp. (such as *Shigella dysenteriae, Shigella flexneri, Shigella boydii* and *Shigella sonnei*), *Staphylococcus* sp. (such as *Staphylococcus aureus, Staphylococcus epidermidis, Staphylococcus hemolyticus, Staphylococcus saprophyticus*), *Streptococcus* sp. (such as *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotope 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae, Streptococcus mutans, Streptococcus pyogenes*, Group A streptococci, *Streptococcus pyogenes*, Group B streptococci, *Streptococcus agalactiae*, Group C streptococci, *Streptococcus anginosus, Streptococcus equismilis*, Group D streptococci, *Streptococcus bovis*, Group F streptococci, and *Streptococcus anginosus* Group G streptococci), *Spirillum minus, Streptobacillus moniliformi, Treponema* sp. (such as *Treponema carateum, Treponema petenue, Treponema pallidum* and *Treponema endemicum, Tropheryma whippelii, Ureaplasma urealyticum, Veillonella* sp., *Vibrio* sp. (such as *Vibrio cholerae, Vibrio parahemolyticus, Vibrio vulnificus, Vibrio parahaemolyticus, Vibrio vulnificus, Vibrio alginolyticus, Vibrio mimicus, Vibrio hollisae, Vibrio fluvialis, Vibrio metchnikovii, Vibrio damsela* and *Vibrio furnisii*), *Yersinia* sp. (such as *Yersinia enterocolitica, Yersinia pestis*, and *Yersinia pseudotuberculosis*) and *Xanthomonas maltophilia* among others.

Bead: An insoluble structure having volume and one or more surfaces. Some bead surfaces can be modified to include a reactive functional group, including but not limited to alcohol, halide, aldehyde, epoxide, amine, azide, alkyne, tetrazine, maleimide, ester, thiol, disulfide, sulfonyl halides or esters such that a covalent bond may be formed. Other bead surfaces have non-fouling properties and may not be easily modified. Beads may have regular or irregular shapes.

Binding or stable binding: An association between two substances or molecules, such as the hybridization of one nucleic acid molecule to another (or itself), the association of an antibody with a peptide, or the association of a protein with another protein or nucleic acid molecule. An oligonucleotide molecule binds or stably binds to a target nucleic acid molecule if a sufficient amount of the oligonucleotide molecule forms base pairs or is hybridized to its target nucleic acid molecule, to permit detection of that binding. "Preferentially binds" indicates that one molecule binds to another with high affinity, and binds to heterologous molecules at a low affinity.

Binding can be detected by any procedure known to one skilled in the art, such as by physical or functional properties of the target complex. For example, binding can be detected functionally by determining whether binding has an observable effect upon a biosynthetic process such as expression of a gene, DNA replication, transcription, translation, and the like. Methods of detecting binding of an antibody to a protein can include known methods of protein detection, such as Western blotting.

Cartridge: A removable component used for various aspects of sample processing. Cartridges can be used for sample analysis. Examples include a single assay cartridge for *Listeria* spp. and a multiplexed cartridge for *Salmonella* and *E. coli*. Cartridges can be used for system functions, including but not limited to sanitation, priming, transportation, storage and calibration.

Contacting: Placement in direct physical association, including both a solid and liquid form.

Detecting: Identifying the presence, absence or relative or absolute amount of the object to be detected.

Epitope: An antigenic determinant. These are particular chemical groups or peptide sequences on a molecule that are antigenic, such that they elicit a specific immune response. An aptamer can bind to an epitope on a surface, such as a cell wall, of a particular pathogen or an antibody can bind to a particular antigenic epitope, such as an epitope of on the surface of a pathogen.

Expression: The process by which the coded information of a gene is converted into an operational, non-operational, or structural part of a cell, such as the synthesis of a protein. Gene expression can be influenced by external signals. For instance, exposure of a cell to a hormone may stimulate expression of a hormone-induced gene. Different types of cells can respond differently to an identical signal. Expression of a gene also can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced.

The expression of a nucleic acid molecule can be altered relative to a normal (wild type) nucleic acid molecule. Alterations in gene expression, such as differential expression, include but are not limited to: (1) overexpression; (2) underexpression; or (3) suppression of expression. Alternations in the expression of a nucleic acid molecule can be associated with, and in fact cause, a change in expression of the corresponding protein.

Protein expression can also be altered in some manner to be different from the expression of the protein in a normal (wild type) situation. This includes but is not necessarily limited to: (1) a mutation in the protein such that one or more of the amino acid residues is different; (2) a short deletion or addition of one or a few (such as no more than 10-20) amino acid residues to the sequence of the protein; (3) a longer deletion or addition of amino acid residues (such as at least 20 residues), such that an entire protein domain or sub-domain is removed or added; (4) expression of an increased amount of the protein compared to a control or standard amount; (5) expression of a decreased amount of the protein compared to a control or standard amount; (6) alteration of the subcellular localization or targeting of the protein; (7) alteration of the temporally regulated expression of the protein (such that the protein is expressed when it normally would not be, or alternatively is not expressed when it normally would be); (8) alteration in stability of a protein through increased longevity in the time that the protein remains localized in a cell; and (9) alteration of the localized expression of the protein (such that the protein is not expressed where it would normally be expressed or is expressed where it normally would not be expressed), each compared to a control or standard. Controls or standards for comparison to a sample, for the determination of differential expression, include samples believed to be normal as well as laboratory values (e.g., range of values), even though possibly arbitrarily set, keeping in mind that such values can vary from laboratory to laboratory.

Laboratory standards and values can be set based on a known or determined population value and can be supplied in the format of a graph or table that permits comparison of measured, experimentally determined values.

Fungal pathogen: A fungus that causes infection or disease. Examples of fungal pathogens include without limitation *Trichophyton rubrum, T. mentagrophytes, Epidermophyton fluccosum, Microsporum canis, Pityrosporum orbiculare* (*Malassezia furfur*), *Candida* sp. (such as *Candida albicans*), *Aspergillus* sp. (such as *Aspergillus fimigatus, Aspergillus flavus* and *Aspergillus clavatus*), *Cryptococcus* sp. (such as *Cryptococcus neoformans, Cryptococcus gattii, Cryptococcus laurentii* and *Cryptococcus albidus*), *Histoplasma* sp. (such as *Histoplasma capsulatum*), *Pneumocystis* sp. (such as *Pneumocystis jirovecii*), and *Stachybotrys* (such as *Stachybotrys chartarum*) among others.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as base pairing. More specifically, A will hydrogen bond to T or U, and G will bond to C. In RNA molecules, G also will bond to U. Complementary refers to the base pairing that occurs between two distinct nucleic acid sequences or two distinct regions of the same nucleic acid sequence.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ concentration) of the hybridization buffer will determine the stringency of hybridization. Calculations regarding hybridization conditions required for attaining particular degrees of stringency are discussed by Sambrook et al. (ed.), *Molecular Cloning: A Laboratory Manual,* 2nd ed., vol. 1-3, Cold Spring Harbor Laboratory Press, Cold Spring Harbor, NY, 1989, chapters 9 and 11, herein incorporated by reference.

Isolated: An "isolated" biological component (such as a nucleic acid molecule, protein, or cell) has been substantially separated or purified away from other biological components in the cell of the organism, or the organism itself, in which the component naturally occurs, such as other chromosomal and extra-chromosomal DNA and RNA, proteins and cells. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules and proteins. The term "isolated" or "isolating" also includes separation or purification of one of more biological components from inorganic and organic material. The terms "isolating" and "capturing" are used interchangeable herein.

Label or Detectable Moiety: A composition detectable by spectroscopic, photochemical, biochemical, immunochemical, electromagnetic, or chemical means. For example, useful labels include radiolabels such as $^{32}P$, $^{35}S$, or $^{125}I$; heavy isotopes such as $^{15}N$ or 13C or heavy atoms such as selenium or metals; fluorescent dyes; chromophores, electron-dense reagents; enzymes that generate a detectable signal (e.g., alkaline phosphatase or peroxidase, as commonly used in an ELISA); or spin labels. The label or detectable moiety has or generates a measurable signal, such as a radioactive, chromogenic, or fluorescent signal, that can be used to quantify the amount of bound detectable moiety in a sample. The detectable moiety can be incorporated in or attached to a molecule (such as a protein, for example, an antibody) either covalently, or through ionic, van der Waals or hydrogen bonds, e.g., or by incorporation of labeled precursors. The label or detectable moiety may be directly or indirectly detectable. Indirect detection can involve the binding of a second directly or indirectly detectable moiety to the detectable moiety. For example, the detectable moiety can be the ligand of a binding partner, such as biotin, which is a binding partner for streptavidin, which can be linked to a directly detectable label. The binding partner may itself be directly detectable, for example, an antibody may be itself labeled with a fluorescent molecule. The binding partner also may be indirectly detectable, for example, it may be bound by another moiety that comprises a label. Quantitation of the signal is achieved by any appropriate means, e.g., fluorescence detection, spectrophotometric detection (e.g., absorption at a particular wavelength), scintillation counting, mass spectrometry, densitometry, or flow cytometry. Methods for labeling and guidance in the choice of labels appropriate for various purposes are discussed for example in Sambrook et al. (Molecular Cloning: A Laboratory Manual, Cold Spring Harbor, New York, 1989) and Ausubel et al. (In Current Protocols in Molecular Biology, John Wiley & Sons, New York, 1998).

Measure: To detect, quantify or qualify the amount (including molar amount), concentration or mass of a physical entity or chemical composition either in absolute terms in the case of quantifying, or in terms relative to a comparable physical entity or chemical composition.

Pathogen: Anything that can produce disease. In some examples, a pathogen is an infectious molecule. In some examples, the pathogen is a live pathogen, such as one or more disease producing organism, such as bacteria, fungi, protozoa and/or worms. In some examples, a pathogen is one or more of a virus, bacteria, fungus, protozoa, worm, protein and/or peptide that is present in a sample obtained from food, water, environment, soil, plant, animal, insect, or human.

Purified: The term "purified" does not require absolute purity; rather, it is intended as a relative term. Thus, for example, a purified protein preparation is one in which the protein referred to is more pure than the protein in its natural environment within a cell. For example, a preparation of a protein is purified such that the protein represents at least 50% of the total protein content of the preparation. Similarly, a purified mRNA preparation is one in which the mRNA is more pure than in an environment including a complex mixture of nucleic acid molecules.

Real-Time PCR (qPCR): A method for detecting and measuring products generated during each cycle of a PCR, which are proportionate to the amount of template nucleic acid prior to the start of PCR. The information obtained, such as an amplification curve, can be used to determine the presence of a target nucleic acid and/or quantitate the initial amounts of a target nucleic acid sequence. Exemplary procedures for qPCR can be found in "Quantitation of DNA/RNA Using Real-Time PCR Detection" published by Perkin Elmer Applied Biosystems (1999); *PCR Protocols* (Academic Press, New York, 1989); *A-Z of Quantitative PCR*, Bustin (ed.), International University Line, La Jolla, CA, 2004; and *Quantitative Real-Time PCR in Applied Microbiology*, Filion (Ed), Caister Academic Press, 2012.

In some examples, the amount of amplified target nucleic acid is detected using a labeled probe, such as a probe labeled with a fluorophore, for example a TAQMAN® probe. In other examples, the amount of amplified target nucleic acid is detected using a DNA intercalating dye. The increase in fluorescence emission is measured in real-time, during the course of the qPCR. This increase in fluorescence emission is directly related to the increase in target nucleic acid amplification. In some examples, the change in fluorescence (Delta Rn; dRn; ΔRn) is calculated using the equation $dRn=Rn^{+}-Rn^{-}$, with $Rn^{+}$ being the fluorescence emission of the product at each time point and $Rn^{-}$ being the fluorescence emission of the baseline. The dRn values are plotted against cycle number, resulting in amplification plots for each sample. The threshold cycle (Ct) is the PCR cycle number at which the fluorescence emission (dRn) exceeds a chosen threshold, which is typically 10 times the standard deviation of the baseline (this threshold level can, however, be changed if desired).

The threshold cycle is when the system begins to detect the increase in the signal associated with an exponential growth of PCR product during the log-linear phase. This phase provides information about the reaction. The slope of the log-linear phase is a reflection of the amplification efficiency. The efficiency of the reaction can be calculated by the following equation: $E=10^{(-1/slope)}$, for example. The efficiency of the PCR should be 90-100% meaning doubling of the amplicon at each cycle. This corresponds to a slope of −3.1 to −3.6 in the Ct vs. log-template amount standard curve.

Sample: An aqueous solution or suspension used in analysis or testing. In some examples, a sample may contain food, water or environmental material. In some examples, a sample may contain biological material, such as urine, saliva, sputum, feces, semen, and other bodily fluids and tissues. In some examples, the material may be preprocessed such as by adding an aqueous solution and paddle blending or by isolating, concentrating or removing material such as through centrifugation or filtering. A sample may contain matter including, but not limited to microorganisms (e.g., bacteria, viruses and fungi), insect, plant, animal, and/or fecal material.

Sensitivity and specificity: Statistical measurements of the performance of a binary classification test. Sensitivity measures the proportion of actual positives which are correctly identified) e.g., the percentage of samples that are identified as including nucleic acid from a particular pathogen). Specificity measures the proportion of negatives which are correctly identified (e.g., the percentage of samples that are identified as not including nucleic acid from a particular pathogen).

Solution: A homogeneous mixture of one or more solutes dissolved in a solvent. As used herein, the terms buffer and solution are used interchangeably and the term buffer does not necessarily indicate that the solution has buffering capabilities.

Standard: A substance or solution of a substance of known amount, purity or concentration. A standard can be compared (such as by spectrometric, chromatographic, or spectrophotometric analysis) to an unknown sample (of the same or similar substance) to determine the presence of the substance in the sample and/or determine the amount, purity or concentration of the unknown sample. In one embodiment, a standard is a peptide standard. An internal standard is a compound that is added in a known amount to a sample prior to sample preparation and/or analysis and serves as a reference for calculating the concentrations of the components of the sample. In one example, nucleic acid standards serve as reference values for expression levels of specific nucleic acids. In some examples, peptide standards serve as reference values for expression levels of specific peptides. Isotopically-labeled peptides are particularly useful as internal standards for peptide analysis since the chemical properties of the labeled peptide standards are almost identical to their non-labeled counterparts. Thus, during chemical sample preparation steps (such as chromatography, for example, HPLC) any loss of the non-labeled peptides is reflected in a similar loss of the labeled peptides.

Virus: A microscopic infectious organism that reproduces inside living cells. A virus consists essentially of a core of nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so. In some examples, a virus is a pathogen. Specific examples of viral pathogens include, without limitation; Arenaviruses (such as Guanarito virus, Lassa virus, Junin virus, Machupo virus and Sabia), Arteriviruses, Roniviruses, Astroviruses, Bunyaviruses (such as Crimean-Congo hemorrhagic fever virus and Hantavirus), Barnaviruses, Birnaviruses, Bornaviruses (such as Boma disease virus), Bromoviruses, Caliciviruses, Chrysoviruses, Coronaviruses (such as Coronavirus and SARS), Cystoviruses, Closteroviruses, Comoviruses, Dicistroviruses, Flaviruses (such as Yellow fever virus, West Nile virus, Hepatitis C virus, and Dengue fever virus), Filoviruses (such as Ebola virus and Marburg virus), Flexiviruses, Hepeviruses (such as Hepatitis E virus), human adenoviruses (such as human adenovirus A-F), human astroviruses, human BK polyomaviruses, human bocaviruses, human coronavirus (such as a human coronavirus HKU1, NL63, and OC43), human enteroviruses (such as human enterovirus A-D), human erythrovirus V9, human foamy viruses, human herpesviruses (such as human herpesvirus 1 (herpes simplex virus type 1), human herpesvirus 2 (herpes simplex virus type 2), human herpesvirus 3 (Varicella zoster virus), human herpesvirus 4 type 1 (Epstein-Barr virus type 1), human herpesvirus 4 type 2 (Epstein-Barr virus type 2), human herpesvirus 5 strain AD169, human herpesvirus 5 strain Merlin Strain, human herpesvirus 6A, human herpesvirus 6B, human herpesvirus 7, human herpesvirus 8 type M, human herpesvirus 8 type P and Human Cyotmegalovirus), human immunodeficiency viruses (HIV) (such as HIV 1 and HIV 2), human metapneumoviruses, human papillomaviruses (such as human papillomavirus-1, human papillomavirus-18, human papillomavirus-2, human papillomavirus-54, human papillomavirus-61, human papillomavirus-cand90, human papillomavirus RTRX7, human papillomavirus type 10, human papillomavirus type 101, human papillomavirus type 103, human papillomavirus type 107, human papillomavirus type 16, human papillomavirus type 24, human papillomavirus type 26, human papillomavirus type 32, human papillomavirus type 34, human papillomavirus type 4, human papillomavirus type 41, human papillomavirus type 48, human papillomavirus type 49, human papillomavirus type 5, human papillomavirus type 50, human papillomavirus type 53, human papillomavirus type 60, human papillomavirus type 63, human papillomavirus type 6b, human papillomavirus type 7, human papillomavirus type 71, human papillomavirus type 9, human papillomavirus type 92, and human papillomavirus type 96), human parainfluenza viruses (such as human parainfluenza virus 1-3), human parechoviruses, human parvoviruses (such as human parvovirus 4 and human parvovirus B19), human respiratory syncytial viruses, human rhinoviruses (such as human rhinovirus A and human rhinovirus B), human spumaretroviruses, human T-lymphotropic viruses (such as human T-lymphotropic virus 1 and human T-lymphotropic virus 2), Human polyoma viruses, Hypoviruses, Leviviruses, Luteoviruses, Lymphocytic choriomeningitis viruses (LCM), Marnaviruses, Narnaviruses, Nidovirales, Nodaviruses, Orthomyxoviruses (such as Influenza viruses), Partitiviruses, Paramyxoviruses (such as Measles virus and Mumps virus), Picomaviruses (such as Poliovirus, the common cold virus, and Hepatitis A virus), Potyviruses, Poxviruses (such as Variola and Cowpox), Sequiviruses, Reoviruses (such as Rotavirus), Rhabdoviruses (such as Rabies virus), Rhabdoviruses (such as Vesicular stomatitis virus, Tetraviruses, Togaviruses (such as Rubella virus and Ross River virus), Tombusviruses, Totiviruses, Tymoviruses, Noroviruses, bovine herpesviruses including Bovine Herpesvirus (BHV) and malignant catarrhal fever virus (MCFV), among others.

II. Introduction

The current "gold" standard practice in the food industry employs the culturing of food and environmental samples using enrichment broth designed to specifically grow the target bacteria, followed by cell isolation with one or more buffer exchanges, often accomplished with centrifugation, cell lysis and DNA or RNA extraction, reverse transcription from RNA to cDNA if RNA is to be utilized, purification to remove substances that may inhibit or otherwise negatively impact amplification, and analysis using PCR or isothermal amplification to amplify and detect pathogen DNA or cDNA. In the absence of the culturing process, the specificity and reliability of commercial, off-the-shelf nucleic acid amplification kits is insufficient. Reliable amplification involves identifying small DNA sequences that are unique to the target organism. The varied and immense biodiversity in food or environmental samples precludes reliable specific amplification. Samples can contain microorganisms, such as bacteria, viruses and fungi, as well as insect, plant, animal, and fecal material. Each of these can have DNA sequences with millions of bases. Many organisms are unknown as are the sequences for every possible genotype or serotype of every species. It is difficult if not impossible to define a DNA sequence that would only bind to a specific sequence in a target pathogen with the knowledge that it would not bind to a DNA sequence that could be present in food or environmental samples. In addition, the presence of compounds such as chlorophyll and humic acids, components of which can inhibit nucleic acid amplification and confound interpretation of results (due to baseline drift, for example). Further, nucleic acid amplification works equally well on dead cells as live cells as long as the nucleic acid sequences are not degraded. Detection of only live cells is required in the food industry since "kill steps", such as sanitation, pasteurization, or cooking can kill pathogens without degrading the pathogen nucleic acid.

Culturing addresses the challenge of detecting relatively low pathogen cell copy counts in large biodiverse samples by increasing the population of the target pathogens in the media. Culturing significantly reduces the biodiversity in the sample since only bacteria and fungi will multiply in the process. Culturing also enables live cell analysis since only live cells will multiply during this process. It also effectively dilutes many nucleic acid amplification inhibitors however, other matrix-associated contaminants may remain, which are sources of inhibitors for downstream enzymatic applications. For example, humic acid, commonly found in soils and agricultural products, has proved challenging to eliminate, since it can easily be co-extracted along with the target DNA. Humic acid is implicated as a strong nucleic acid amplification inhibitor through sequence specific DNA binding.

Enrichment broth is designed to favor growth of target organisms over competing non-targeted organisms. Creating enrichment broths that significantly favor specific target organisms can be very challenging and costly. For example, enrichment broths designed for *Escherichia coli* O157:H7 can range greatly in specificity and cost. The least specific broths can lack the specificity to prevent significant false positives while the most specific broths can be deemed too expensive for daily food analysis. In addition, it is often not possible or practical to create a broth that can enrich multiple different pathogens with sufficient specificity. During the exponential growth phase of the culturing process, the number of bacteria can double every twenty minutes. Depending on numerous factors, millions, billions or even trillions of cells may be required for reliable detection. As such, the culturing process can require up to a one-day time period or more, delaying analysis. Cells that have been stressed, such as by exposure to chemicals, such as chlorine, antimicrobials, or low temperature may take even longer to reach the exponential growth phase. It is generally not practical to increase the culture time for all pathogen analysis sufficiently to ensure reliable growth of all cells.

Food industry sample size and collection methods are the result of 40 years of industry experience and data analysis. It is highly desirable that pathogen analysis utilize these established sample volumes and collection methods. Environmental samples can be obtained using stick-mounted sponges such as the 3M Sponge-Stick, typically pre-wetted with 10 mL of neutralizing buffer. After collection, 90 mL of buffer (typically, growth medium) is added to a filter bag and the sponge is processed in a paddle blender, such as the Seward Stomacher, for 2-3 minutes to release the pathogen cells into the buffer. Compared to standard sample collection and paddle blending methods used by the food industry, the disclosed process utilizes a different paddle blending buffer composition. In comparison to the enrichment broth used as a buffer for traditional culture-based detection, the disclosed system utilizes buffered saline which can be less costly.

To reliably process environmental samples, the disclosed system ensures sufficient filter load capacity, consistently captures target cells, and removes substances that can interfere or inhibit nucleic acid amplification, such as humic acid and magnesium.

Bacteria cannot be effectively isolated from all food and environmental samples using filtration. These samples can contain a large number of organisms and substances, such as clay particles, that can be the same size as bacteria. The inventors have developed a flow-through assay that captures bacteria without the need for small particle filtering. Capture time in an aptamer-based or antibody-based cell capture is influenced by the distance between the cells and the capture molecule. Reducing the distance decreases the time for all cells to be captured. Capture time in a flow-through system is a function of the height of the flow channel, the flow rate, and the surface area of the capture surface along the flow path. The disclosed surface chemistry works on numerous surfaces including but not limited beads, slides and other glass surfaces, such as any surface containing soda-lime glass. Soda-lime glass is one of the least expensive and most commonly used glass types. Soda-lime glass is used for commodity beverage bottles, windowpanes and in street lane marker paint to make them reflective. As such, one can massively increase capture surface size without a material increase in cost. The inventors have demonstrated high binding efficiency in prototype flow channels flowing at 10 milliliters or 15 milliliters per minute. They have shown the capability to increase the flow rate without loss in capture efficiency by simply increasing the diameter of the flow channel. By extrapolating the experimental results, it should be possible to efficiently capture cells with flow rates in liters per minute, tens of liters per minute or greater. This is of great benefit for applications with large sample volumes such as water, soil and food testing. The channel size can alternatively be reduced for applications where size and portability are desired, such as point-of-care diagnostics. The disclosed system and method are believed to provide the ideal process for rapid, low cost capture of pathogen cells in food, environmental and other samples.

Culture-independent analysis of foodborne pathogens meeting all critical food industry requirements has never before been successfully accomplished prior to this disclosure. Foodborne pathogen analysis needs to detect as few as 1 pathogen cells per milliliter of large, biodiverse samples that can be challenging to process. Analysis should detect only live cells in order to verify the effectiveness of "kill steps" such as sanitation, pasteurization, or cooking (steps which typically do not materially alter cell RNA or DNA). It has been assumed that because bacterial transcripts are sensitive to degradation by intra- and extra-cellular RNases, mRNA levels should rapidly decline after death. Therefore, unlike DNA-based detection, mRNA would only be limited to the viable and active cells within the population. It has been found that RNA-based detection cannot be used to accurately enumerate living cells (see, for example, frontiersin.org/articles/10.3389/fmicb.2016.00223/full #B32, which is hereby incorporated by reference in its entirety). As such, a new method is needed to detect only live cells. The test process ideally is automated, usable by minimally trained personnel and cost effective. The disclosed system and method achieve all of these requirements and was validated in blind testing with 100% correct results (see Example Section).

The disclosed system and method also provide results that are quantitative; key information when identifying and isolating the source of a contamination. The Food Safety Modernization Act (FSMA) was signed into law in January 2011. Its aim is to ensure the U.S. food supply is safe by shifting focus from responding to foodborne contamination to that of preventing it. Rapid detection of pathogens can facilitate compliance with FSMA by accelerating identification and confirming the presence of pathogens. The disclosed system and method enable proactive prevention and process change, allowing for corrective action prior to food entering the supply chain.

It is believed that the disclosed system and method can significantly reduce or eliminate the food industry's test and hold cycles, enabling significant cost savings through improved operational efficiencies and reduced labor, transportation, and storage needs. The public, through retail and food service channels, can see safer product entering the supply chain faster, with greater shelf life, and the potential for better, more complete traceability. The disclosed rapid pathogen detection platform could help reduce the economic burden to food processors and safeguard the public. Reducing the reaction time to identify, qualify, and eradicate foodborne pathogen contaminations reduces the number of people impacted. Thus, the disclosed system and method provide, for the first time, quantitative results to help food safety professionals measure the effectiveness of food safety processes. The technology also enables testing in the field, allowing for portable analysis in growing regions and for pathogen testing at US ports and borders.

III. System and Method for Detecting and Monitoring Pathogens

Disclosed herein is a system/platform, kit and method for rapid pathogen detection, quantitation and monitoring, including detecting, quantitating and monitoring bacterial, fungal and viral foodborne pathogens. The disclosed system and method have the ability to isolate only live cells, not dead cells which is advantageous. In embodiments, the disclosed system does not isolate cells that have been killed from heat and exposure to certain antimicrobial substances. For example, in some embodiments, the disclosed system and method result in less than 0.1%, such less than 0.01%, less than 0.001% or less of cells that have been killed from heat and exposure being detected. In embodiments, the disclosed systems and methods capture, release and process sufficient live cells to enable detection from a typical sample size of 90 milliliters or larger without requiring cell culture.

In some examples, the isolation conditions include reducing the concentration of sodium to preclude the capture of dead cells and adjusting the composition of the solution and conditions. In some examples, the isolation conditions include reducing the temperature of hybridization. In some examples, magnesium is introduced to stabilize the aptamer formation with reduced temperature. In some examples, the temperature is reduced to stabilize the DNA backbone of the aptamer structure. In some examples, a temperature of less than 20 degrees Celsius is used as the lower temperatures is associated with decreased or no dead cells binding. In some examples, the magnesium is present at a concentration sufficient to increase aptamer melting temperatures to result in desired secondary structure formation while in the presence of less than 100 mM sodium and less than 20 degrees Celsius. In some examples, the magnesium concentration is more than 0.1 mM. In some examples, the isolation of live cells is performed in the presence of one or more of the following: (1) more than 0.1 mM of magnesium, such as between 0.1 mM and 100 mM, 0.1 mM and 10 mM, 0.1 mM and 5 mM, 0.2 mM and 1 mM, including 0.1 mM, 0.2 mM, 0.3, mM, 0.4 mm, 0.5 mM, 0.6 mM, 0.7 mM, 0.8 mM, 0.9 mM, 1 mM, 2 mM, 3 mM, 4 mM, 5 mM, 6 mM, 7 mM, 8 mM, 9 mM or 10 mM; (2) in the presence of less than 100 mM $Na^+$ (sodium), such as between 100 mM and 1 mM, 100 mM and 10 mM, including 100 mM, 90 mM, 80 mM, 70 mM, 60 mM, 50 mM, 40 mM, 30 mM, 20 mM, 10 mM, 5 mM or 1 mM; and/or (3) at less than 20 degrees Celsius, such as between 20 and 0 degrees Celsius, between 20 and 2 degrees Celsius, between 12 and 9 degrees, between 11 and 9 degrees, including 20 degrees Celsius, 19 degrees Celsius, 18 degrees Celsius, 17 degrees Celsius, 16 degrees Celsius, 15 degrees Celsius, 14 degrees Celsius, 13 degrees Celsius, 12 degrees Celsius, 11 degrees Celsius, 10 degrees Celsius, 9 degrees Celsius, 8 degrees Celsius, 7 degrees Celsius, 6 degrees Celsius, 5 degrees Celsius, 4 degrees Celsius, 3 degrees Celsius, 2 degrees Celsius, 1 degree Celsius. In some examples, the magnesium is present at a concentration sufficient to increase the aptamer melting temperatures to result in the desired secondary structure formation while in the presence of less than 100 mM sodium and less than 20 degrees Celsius. In some examples, the isolation conditions are performed in the presence of 1× phosphate buffer saline (PBS) solution which contains approximately 150 mM of sodium. In some examples, the isolation conditions are performed in the presence of 0.2× PBS solution which contains approximately 30 mM sodium. In some examples, the isolation conditions are performed in the presence of approximately 0.75×PBS solution which contains approximately 100 mM sodium. In some examples, the disclosed method and system utilize a pathogen capture column containing of beads that are functionalized with aptamers with affinity to the pathogen of interest and through which sample is flowed to bind to the functionalized bead surface. In some examples, the beads are functionalized with more than one aptamer. In some examples, the beads are retained within the column by a filter, such as a stainless steel mesh, having a pore size smaller than the size of the beads. In some examples the container of beads comprises a pipe of uniform cross section. In some examples, cross-sectional area of the pathogen capture column is constant. In some examples, the cross-sectional area of the pathogen capture column varies. In some examples, capturing one or more live pathogens comprises applying the sample to a pathogen-isolation column containing multiple beads of one or more sizes. In some examples, the pathogen capture column is of a uniform shape, such as of a circle, oval or polygon. In some examples, the cross-section of the pathogen capture is a non-uniform shape.

The disclosed system and method are cell culture-independent and utilize a two-stage process which increases the specificity of detection. Specifically, the method involves use of pathogen isolation, such as pathogen cells, isolation and release as a first step followed by nucleic acid extraction and detection as a second step. In some examples, the two-step process includes pathogen isolation, such as pathogen cell isolation, accomplished via aptamer-based or antibody-antigen capture. In some examples, the two-step process includes cell isolation accomplished by antibody/antigen cell capture. In some examples, the two-step process involves the nucleic acid detection being performed by numerous methods including but not limited to polymerase chain reaction, isothermal amplification, hybridization detection, and sequencing. In some examples, the disclosed two-step process involves including sample, such as cells, washing in the pathogen isolation process to reduce/eliminate the need for purification at the nucleic acid level. In some examples, the two-step process includes multiple steps to concentrate the pathogen, such as pathogen cells and/or nucleic acids including pathogen isolation on a surface, such as on beads in a column, cell wash, cell release, cell capture on filter, cell release. It is contemplated that a surface can be on a bead, fiber, rods powders or other material capable of performing as a substrate. In some embodiments, the surfaces, such as bead surfaces, are primarily comprised of a material that has been modified for aptamer or antibody attachment, such as via reactive functional surface group or combination of functional surface groups (including, but not limited to alcohol, aldehyde, epoxide, amine, functionalization via click chemistry, cyclic diene, and/or covalent linkages). In some embodiments, non-covalent attachment is employed. It is contemplated that surface attachment of functionalized molecules can be established by methods known to one of skill in the art (see, for example, www.idtdna.com/pages/products/custom-dna-rna/oligo-modifications, sfvideo.blob.core.windows.net/sitefinity/docs/default-source/technical-report/attaching-oligos-to-solid-supports.pdf?sfvrsn=47483407_6 or www.gelest.com/wp-content/uploads/Hydrophobicity-Hydrophilicity_and_Silane_Surface_Modification.pdf, which are each incorporated by reference in each of the entirety as available on Jul. 16, 2020). Insoluble substrates, such as insoluble beads, can be surface functionalized with chemical groups that react with cell capture agents. These functional groups include, but are not limited alcohol, halide, N-hydroxy succinimide (NHS) esters, isocyanates, isothiocyanates, benzoyl fluoride, iodoacetamide, 2-thiopyridine, diazonium salts, arylamine, phosphoesters, ketone, hydrazide, cycloalkyne, trialkyl halosilane, trimethoxy halosilanes, trialkoxy halosilanes aldehyde, epoxide, amine, azide, alkyne, tetrazine, maleimide, ester, thiol, disulfide, sulfonyl halides or esters. In some embodiments, aptamers, antibodies or other cell capture agents are modified to include a reactive functional group, including but not limited to alcohol, halide, aldehyde, epoxide, amine, azide, alkyne, tetrazine, maleimide, ester, thiol, disulfide, sulfonyl halides or esters such that a covalent bond is formed that will not break during subsequent steps of the cell capture and identification process. Appropriate modification of the cell capture agent depends on the surface modification, such as bead surface modification. For example, an insoluble substrate, such as insoluble bead, functionalized with alcohol can react with cell capture agent modified to include an ester or epoxide. Similarly, an insoluble bead functionalized with an azide can react with a cell capture agent modified as an alkyne, or vice versa. In some embodiments, a modification is made to add or increase the hydroxyl groups in a polymer. In some examples, one or more linkers, such as thiol, biotin/streptavidin, or click chemistry is used.

In some examples, the disclosed two-step process includes a flow-through process. In some embodiments, releasing the one or more captured live pathogens from aptamers or antibodies is performed by using a flow rate equal to or higher than the flow rate used to capture the one or more pathogens. In some embodiments, the flow rate for releasing the one or more captured live pathogens is the same flow rate as for pathogen capture. In some embodiments, the flow rate for releasing the one or more captured live pathogens is at least 2×, such as about 2×, 3×, 4×, 5×, or 10× higher than the flow rate for capturing the one or more pathogens. In some embodiments, the flow rate for releasing the one or more captured live pathogens is at least 10% higher than the flow rate for capturing, In some examples, the disclosed two-step process involves nucleic acid detection, wherein the nucleic acid detected is one or more of DNA or RNA. In some examples, the disclosed two-step process allows for one or more different cell types to be isolated in which the different cells can bind to an aptamer or antibody and where multiple different aptamers or antibodies are used to isolate different cells. In some examples, the disclosed two-step process can detect multiple nucleic acid sequences. For example, the nucleic acid extraction can be preceded by release of cells from aptamers or antibodies prior to nucleic acid extraction. In some examples, the disclosed system and method involve a culture-independent process of isolate, wash, release, extract, nucleic acid detection. It is contemplated that conditions leading to release of captured pathogen may depend on the pathogen (e.g., target) and the aptamer or antibody (e.g., probe). For example, conditions can be conducted at a relatively neutral pH, such as between 6.8 and 7.2 pH, resulting in reduced binding affinities conducive to cell release at very high or very low pHs. In embodiments, a release buffer includes a combination of 1M NaCl, 100 mM EDTA, 0.1% Tween 20, 0.05% SDS, 30 mM $NaHCO_3$, pH 10.3-10.4. It is contemplated that known methods of aptamer or antibody release can be employed as well (see, for example, US Patent Publication US20120258870, Zhu et al., IET Nanobiotechnol. 2014 March; 8(1): 2-9; Bellaperche and DeRosa, Pharmaceuticals 2018, 11, 80; doi: 10.3390/ph11030080, each of which is hereby incorporated by reference in its entirety). For example, aptamer release can be achieved by manipulating various factors or combinations of factors including, but not limited to temperature (see Bellaperche and DeRosa, Pharmaceuticals 2018, 11, 80; doi:10.3390/ph11030080 which is hereby incorporated by reference for such teachings), solution composition such as pH (see, Zhu et al., IET Nanobiotechnol. 2014 March; 8(1): 2-9, which is hereby incorporated by reference for such teachings), surfactants such as but not limited to Triton, polysorbate, and other substances such as, but not limited to chelators such as but not limited to EDTA. For example, aptamer design and selection (e.g., via Selex or similar process) is to be conducted at close to neutral pH, resulting in reduced binding affinities conducive to cell release at very high or very low pHs. In embodiments, cell release from antibodies can be accomplished through methods known to one of skill in the art as well as through the use of various agents and varying temperature, such as varying temperature (heat), and/or solution composition (e.g., EDTA; Asian J Transfus Sci. 2013 January-June; 7(1): 29-32.
doi: 10.4103/0973-6247.106727, which is hereby incorporated by reference). Similarly, cell release from various surfaces, including substrates disclosed herein can be facilitated by the use of surfactants and chelators, such as, but not limited to EDTA.

In some examples, the disclosed method and system utilize a pre-filter comprised of a column of beads to remove large particles prior to a cell isolation stage. For example, the beads in the pre-filter contain similar or smaller size than the larger beads in the cell isolation stage. In some examples, the pre-filter and/or the cell isolation stage contains multiple size beads. In some examples, the beads in the pre-filter have non-fouling surface properties. In some examples, the pre-filter has a funnel-shaped component. In some examples, the pre-filter also acts as a bubble trap to prevent air from reaching the pathogen isolation container. In some embodiments, released cells may be collected in liquid in a vented bubble trap acting as a reservoir and acting to remove air before the cells in liquid are flowed through a filter to collect cells. In some examples, the filter permits concentration of cells and permits washing cells with solution to reduce or remove possible substances) from release solutions(that may or may not interfere with subsequent processes. The solution used to wash concentrated cells is primarily water and may or may not include surfactant, such as, but not limited to polysorbate20) e.g., 0.1% PS20).

In some embodiments, the bubble trap may include at least one inlet port, at least one outlet port, and a vent to air. In some embodiments, the vent is outside of the inlet port. In some embodiments, the bubble trap includes multiple ports, one of which is a vent to air. The vent to air is required and advantageous as it permits the bubble trap to eliminate volumes of air in excess of the volume capacity of the bubble trap from subsequent flow of cells through a filter. In embodiments, the vent may contain sensors) examples include liquid level sensors and bubble sensors(that permit feedback control of the volume of liquid pumped into the bubble trap. Prior systems with bubble traps (see, for example, U.S. Pat. No. 10,232,369) are inadequate for the present system because of their limited capacity for air. These prior systems had no means to vent air directly from the bubble trap, therefore the functional air capacity was limited by the volume. The previous bubble trap also did not have any means to determine when the bubble trap was filled with liquid and/or nucleic acids including cell isolation on beads in a column, cell wash, cell release, cell capture on filter, cell release. The bubble trap in the present system overcomes these limitations of the previous systems by including a vent for air and sensors permitting feedback control.

Figure 8:
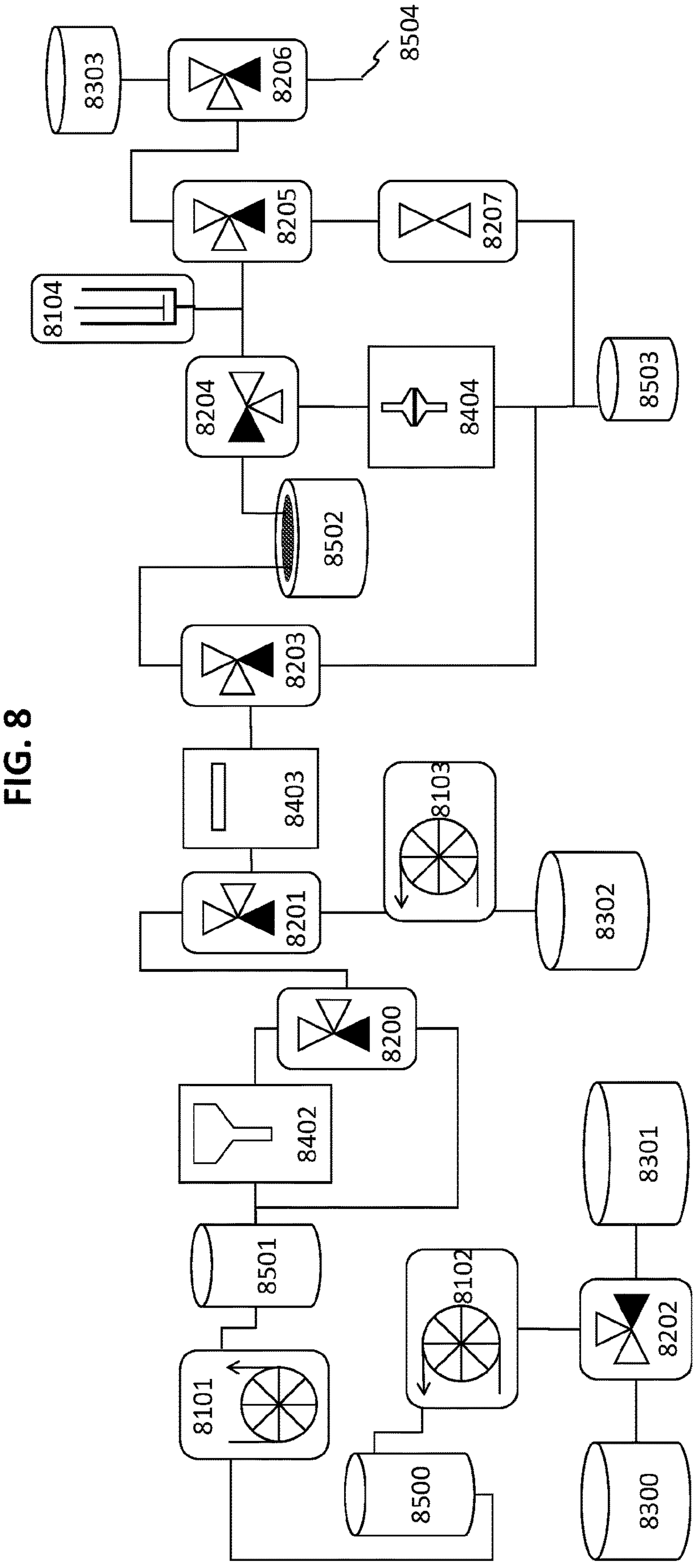
FIG. 8 is a block diagram of a system in accordance with an exemplary embodiment of the disclosure.

Referring to FIG. 8, an exemplary system is shown which includes a first of a sample input chamber 8500, pre-filter 8402, cell capture filter 8403, lysis filter 8404, waste collection 8502 and PCR sample collection tube 8503. The system is inserted into an instrument which comprises a number of further fluidic components. Collectively, a fluidic circuit is formed.

As illustrated, the disclosed system includes a selector valve 8202, such as a 3-way valve. The sample input chamber 8500 is connected to pump 8102 on the instrument, which is connected to the common port of 8202 on the instrument. In operation, port 8202 is generally in an open position and connected to the wash buffer reservoir 8300 on the instrument and sanitation buffer reservoir 8301 on the instrument and is used to select between the sanitation buffer reservoir 8301 and the wash buffer reservoir 8300.

In a disclosed system, an output of 8501 is connected to pump 8101 on the instrument, which is then connected to tube heat exchanger 8501, before entering pre-filter 8402 on the device. The output of the pre-filter is connected to common port of a pre-filter bypass valve 8200. In operation, port 8202 is generally in a closed position and connected to an inlet of 8401. In operation, a port of pre-filter bypass valve 8200 is connected to the normally open port of valve 8201. The normally closed port of valve 8201 is connected to a peristaltic pump 8103. The inlet of 8103 is connected to the release buffer reservoir 8302. The common port of valve 8201 is connected to the cell capture filter 8403.

In an embodiment, the output of 8403 is connected to the common port of valve 8203. The normally open port of 8203 is connected waste reservoir 8502. The normally closed port of 8203 is connected to the bottom of lysis filter 8404. The top of 8404 is connected to the normally open port of valve 8204. The normally closed port of 8204 is connected to waste reservoir 8502. The normally open port of 8204 is connected to syringe pump 104. The outlet of 8104 is also connected to the common port of valve 8205. The normally open port of valve 8206 is connected to lysis buffer reservoir 8303. The normally closed port of valve 8206 is open to a filtered air inlet 8504. The normally closed port of valve 8205 is connected to valve 8207. The outlet of 8207 port is connected to the outlet of 8404. PCR sample collection tube 8503 is also connected to the bottom of 8404.

In use, a disclosed system can be primed with buffers prior to use or as part of the first use. An exemplary method of detecting and monitoring includes pre-filter and capture column conditioning prior to loading a sample. Valves 8200, 8201, 8202 and 8203 are unpowered. Pump 8102 is powered, drawing fluid from the wash buffer reservoir 8300 through valve 8202 and into the sample reservoir 8500. Pump 8102 continues to pump, drawing fluid from the wash buffer reservoir 8300 through valve 8202 and into the sample reservoir 8500. Pump 8101 continues to pump, drawing fluid from the sample loading reservoir 8500, and into tubing cooling heat exchanger 8501, valve 8200, valve 8201, cell capture column 8403, valve 8203 and waste reservoir 8502. Pump 8102 is stopped.

In an exemplary embodiment, the method includes loading the sample and capturing the cells. For example, a sample is loaded into sample loading chamber 8500. Valves 8200, 8201, 8202 and 8203 are unpowered. Pump 8101 is powered, drawing fluid from the sample loading reservoir 8500, and into tubing cooling heat exchanger 8501, pre-filter 8402, valve 8200, valve 8201, cell capture column 8403, valve 8203 and waste reservoir 8502. Large particles are trapped in the pre-filter. Target cells are captured in cell capture column 8403.

In an exemplary embodiment, the method includes flushing the remaining sample from the sample loading chamber. Valves 8200, 8201, 8202 and 8203 are unpowered. Pump 8102 is powered, drawing fluid from the wash buffer reservoir 8300 through valve 8202 and into the sample reservoir 8500. Pump 8101 is powered, drawing fluid from the sample loading reservoir 8500, and into tubing cooling heat exchanger 8501, pre-filter 8402, valve 8200, valve 8201, cell capture column 8403, valve 8203 and waste reservoir 8502.

In an exemplary embodiment, the method includes washing captured cells to remove PCR inhibitors and air gap introduced to prevent buffers from mixing. In some embodiments of the method, valves 8201, 8202 and 8203 are unpowered. Valve 8200 is powered to bypass the pre-filter. Pump 8102 continues to pump, drawing fluid from the wash buffer reservoir 8300 through valve 8202 and into the sample reservoir 8500. Pump 8101 continues to pump, drawing fluid from the sample loading reservoir 8500, and into tubing cooling heat exchanger 8501, valve 8200, valve 8201, cell capture column 8403, valve 8203 and waste reservoir 8502. Pump 8102 is stopped. Pump 8101 continues to pump, fluid in the sample loading reservoir 8500 is removed and air is pulled through pump 8101, tube cooling heat exchanger 8501, valve 8200 and through valve 8201 to create an air gap. Pump 8101 is stopped. The method includes introducing an air gap sufficient to (1) prevent or greatly reduce mixing of buffer components (as release performance deteriorates when buffers are mixed) and facilitate efficient release from the capture column. In some examples, an air gap less than 5 mL is created, such as between 1 mL and 5 mL, between 2 mL to 4 mL, 3 mL to 5 mL, 1 mL to 3 mL, including about 1 mL, 2 mL, 3 mL, 4 mL, and 5 mL. It is contemplated that the air gap can be scalable with the dimensions (diameter and/or length) of the capture column. For example, in some embodiments, tubing diameter used within the system and method is about ⅛ inch in diameter and the introduced air gap is less than 5 mL, such as between 1 mL and 5 mL, between 2 mL to 4 mL, 3 mL to 5 mL, 1 mL to 3 mL, 2 mL to 3 mL, including about 1 mL, 2 mL, 3 mL, 4 mL, and 5 mL. In some embodiments, the air gap is sufficient to yield an release efficiency of greater than 10%, greater than 20%, greater than 30%, such as between 10% and 40%, 20% and 40%, 30% and 40%, 30% and 50% or more.

In some examples, a single air gap is introduced to into the system. In some examples, more than one air gap is introduced into the system, such as several smaller air gaps in comparison to one larger air gap.

In an exemplary embodiment, the method includes capturing released cells and trapping in the lysis filter. Valves 8201, 8203 and 8204 are powered and pump 8103 is started. Pump 8103 draws fluid from the release buffer reservoir 8302, through valve 8201, capture column 8403, valve 8203, lysis filter 8404, valve 8204, and into the waste reservoir 8502. Pump 8103 is stopped. Cells are trapped in lysis filter 8404.

In an exemplary embodiment, the method includes exchanging buffer with lysis buffer and then removing the buffer. Valve 8204 is powered and valves 8203 and 8205 are unpowered. Syringe pump 8104 is withdrawn, pulling lysis buffer from the lysis buffer reservoir 8303, through valve 8206 and valve 8205 into syringe pump 8104. Valves 8204 and 8205 are powered, valve 8207 is open, and valve 8203 is unpowered. Syringe pump 8104 is purged, pushing lysis buffer from the syringe pump 8104, through valves 8205 and 8207, through the bottom of the lysis filter, through valve 8204 and into waste reservoir 8502. Valve 8205 is unpowered. Valves 8204 and 8206 are powered. Syringe pump 8104 is withdrawn, pulling air from the air inlet 8504, through valve 8206 and valve 8205, and into the syringe pump 8104. Valve 8204, 8205 are powered and valve 8207 is open. The syringe pump 8104 is purged, pushing air from the syringe pump 8104, through valves 8205 and 8207, through the bottom of the lysis filer, through valve 8204 and into waste reservoir 8502.

In an exemplary embodiment, the method includes back flowing lysis buffer to release cells into removable PCR tube. Valve 8205 is unpowered. Valves 8204 and 8206 are powered. Syringe pump 8104 is withdrawn, pulling air from the air inlet 8504, such as approximately 950 μL of air from the air inlet 8504, through valve 8206 and valve 8205, and into the syringe pump 8104. Valves 8204 is powered and valves 8203, 8205, 8206, and 8207 are unpowered. Syringe pump 8104 is withdrawn, pulling lysis buffer from the lysis buffer reservoir 8303, such as pulling approximately 50 μL of lysis buffer from the lysis buffer reservoir 8303, through valve 8206 and 8205 into syringe pump 8104. Valves 8205 is powered and valves 8203, 8204 and 8207 are unpowered. The syringe pump 8104 is purged, pushing lysis buffer followed by air through valve 8204, through the top of the lysis filter 8404 and into the removable PCR tube 8503.

In some embodiments, the method includes the optional sanitation process. For the optional sanitation process, a sanitation cartridge is inserted and valves 8200, 8202 are powered. Pumps 8101 and 8102 are powered, drawing sanitation buffer from sanitation reservoir 8301 into and from the sample loading reservoir 8500, into tubing cooling heat exchanger 8501, pre-filter 8402, valve 8200, valve 8201, cell capture column 8403, valve 8203 and waste reservoir 8502.

Figure 9:
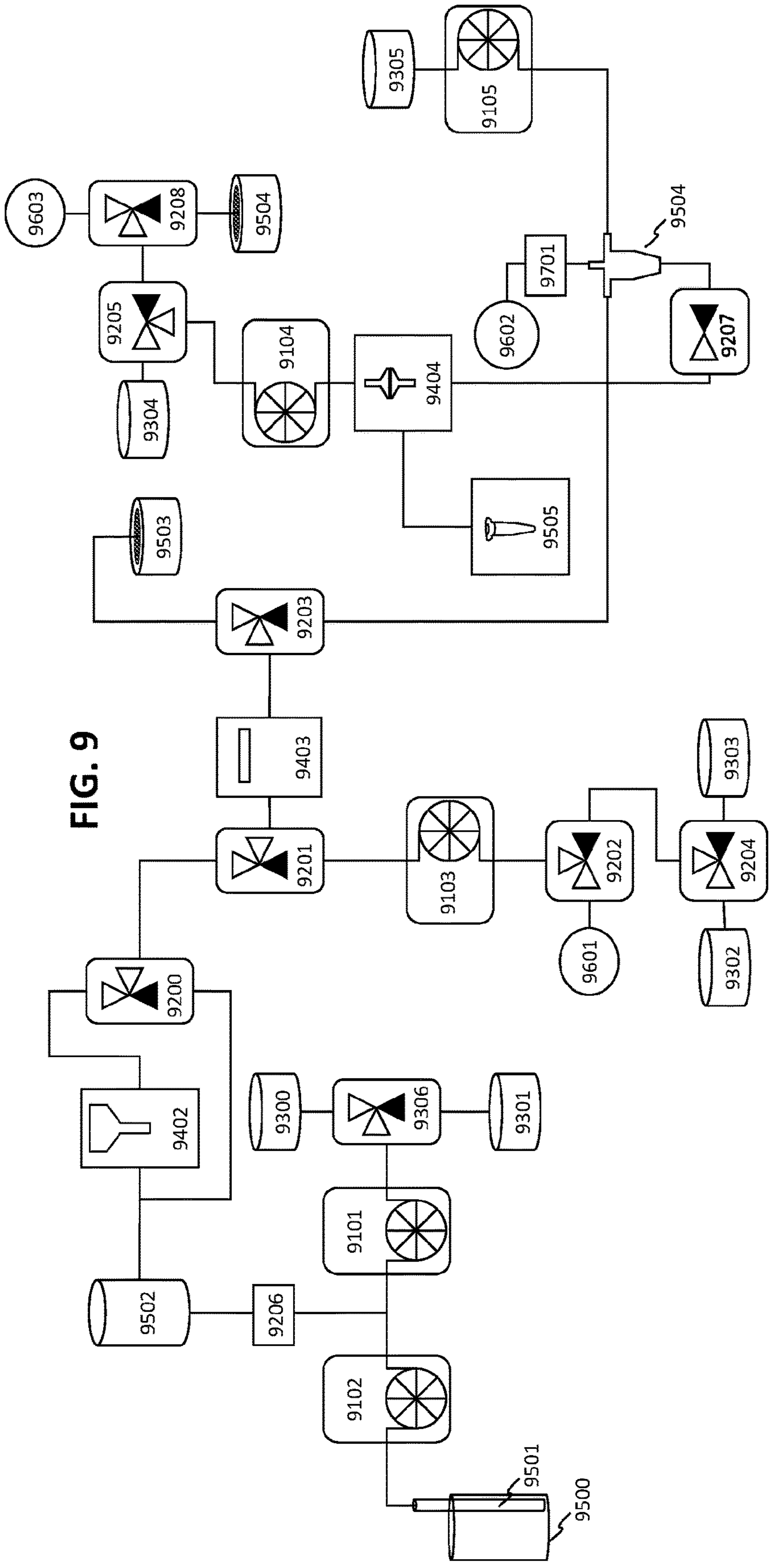
FIG. 9 is a block diagram of a system in accordance with an exemplary embodiment of the disclosure.

Referring to FIG. 9, an exemplary system is shown which includes a sample input source, which can be a temporary or permanent bag or reservoir, 9500, sample input bag straw 9501, pre-filter 9402, cell capture filter 9403, lysis filter 9404, waste collection 9503, bubble trap 9504 and PCR sample collection tube 9505. The system is inserted into an instrument which can include a number of further fluidic components. Collectively, a fluidic circuit is formed.

As illustrated, the disclosed system includes a sample input bag straw 9501 inside sample bag 9500, connected to pump 9102, which is connected to the input of the tube heat exchanger 9502. Selector valve 9206, such as a 3-way valve, is used to select between the wash solution reservoir 9300 on the instrument and sanitation solution reservoir 9301 on the instrument. Selector valves that are in the open position when no power is applied are generally in an open position to conserve power and reduce heat. The common port of valve 9206 is connected to pump 9101 which is connected to the input of the tube heat exchanger 9502 along with pump 9102 after passing through liquid sensor 9702.

In a disclosed system, the output of tube heat exchanger 9502 is connected to the input of pre-filter 9402 and to one port of valve 9200. Valve 9200 is used to select between the output of tube heat exchanger 9502 and the output of pre-filter 9402 on the device. Valve 9201 is used to select between the common port of valve 9200 and the output of pump 9103. The input of pump 9103 is connected to the common port of valve 9202. Valve 9202 selects between filtered air supply 9601 and the common port of valve 9204. Valve 9204 selects between cell release solution reservoir 9302 and wash solution reservoir 9303. The common port of valve 9201 is connected to the cell capture filter 9403.

In an embodiment, the output of 9403 is connected to the common port of valve 9203. The normally open port of 9203 is connected waste reservoir 9503. The typically closed port of 9203 is connected to an input of bubble trap 9504. Lysis solution reservoir 9306 is connected to pump 9105 and pump 9105 is connected to an input of bubble trap 9504. Filtered air supply 9602 connects to an input of bubble trap 9504 after passing through liquid sensor 9701. The output of bubble trap 9504 is connected to and regulated by valve 9208 which is connected to the bottom of lysis filter 9404. The top of lysis filter 9404 is connected to pump 9104. Pump 9104 is connected to the common port of valve 9205. Valve 9205 selects between lysis solution reservoir 9304 and the common port of valve 9208. Valve 9208 selects between waste reservoir 9305 and filtered air supply 9603.

Prior to initial use, prior to system storage between uses, or after use, a disclosed system can be sanitized with solutions prior to subsequent use. An exemplary method involves using a sanitation cartridge, a sample bag and straw, and sanitation solution to allow of sanitation of all the connections among the cartridge components and sanitation of the bubble trap without adversely affecting an analysis cartridge. Valves 9200, 9201, 9203 and 9207 are unpowered. Valve 9206 is powered. Pump 9101 and pump 9102 are powered, drawing fluid from the sanitation solution reservoir 9301 through valve 9206 and into the sample bag or reservoir 9500 via straw 9501. Pump 9102 is stopped. Pump 9101 continues to pump, drawing fluid from sanitation solution reservoir 9301 through valve 9206, and into tubing cooling heat exchanger 9502, into sanitation cartridge prefilter 9402, through valve 9200, valve 9201, cell capture column 9403, valve 9203 and into waste reservoir 9503. Pump 9101 is stopped. Valves 9200 and 9203 are powered (sanitizes prefilter bypass alternate path). Pump 9101 continues, moving sanitation solution through sanitation cartridge alternate path through normally closed valve 9200 port through normally closed Valve 9203 port to bubble trap 9207 until sensor 9701 detects that bubble trap is full. Pump 9101 is stopped. Valves 9203, 9206 and 9207 are powered. Valve 9200 is unpowered.

Following prescribed contact times for sanitation solutions in the system, the sanitation solution is flushed to remove completely from the system using solutions that do not possess bactericidal or other lethal properties to cells and which do not pose contamination risk to the system. These solutions include wash buffer, lysis solution and water.

In an exemplary method, sanitation solution is removed from the bubble trap using pump 9104. Wash buffer from reservoir 9300 is rinsed through the same flow paths to remove sanitizing solution, including twice completely filling the bubble trap 9504 and draining via valve 9207 and sanitizing cartridge "lysis filter" path. An exemplary rinsing method involves using a sanitation cartridge, a sample bag and straw, and wash buffer to allow rinsing of all the connections among the cartridge components and rinsing of the bubble trap without adversely affecting an analysis cartridge. Valves 9200, 9201, 9203, 9206 and 9207 are unpowered. Pump 9101 and pump 9102 are powered, drawing fluid from the wash buffer reservoir 9300 through valve 9206 and into the sample bag or reservoir 9500 via straw 9501. Pump 9102 is stopped. Pump 9101 continues to pump, drawing fluid from wash buffer reservoir 9300 through valve 9206, and into tubing cooling heat exchanger 9502, into sanitation cartridge prefilter 9402, through valve 9200, valve 9201, cell capture column 9403, valve 9203 and into waste reservoir 9503. Pump 9101 is stopped. Valves 9200 and 9203 are powered (rinses prefilter bypass alternate path). Pump 9101 continues, moving wash buffer through sanitation cartridge alternate path through normally closed valve 9200 port through normally closed Valve 9203 port to bubble trap 9207 until sensor 9701 detects that bubble trap is full. Pump 9101 is stopped. Valves 9203, 9206 and 9207 are powered. Valve 9200 is unpowered.

Waste reservoirs monitored to prompt emptying of the waste reservoir before it exceeds capacity. Following sanitation and post-sanitation rinses, the system can be primed using a clean cartridge that is not analysis cartridge.

In an exemplary embodiment, pump 9103 is capable of pumping at the cell release flow rate which is a higher flow rate than the cell capture flow rate as provided by pump 9102.

Priming

In use, a disclosed system can be primed with solutions prior to use or as part of the first use. An exemplary method involves using a different cartridge and a different sample bag and straw for priming, such as a cartridge, sample bag and straw used for sanitation, to allow priming of cell release solution with adversely affecting the cell capture filter and priming the connections between the bubble trap and the lysis filter without adversely affecting the lysis filter.

With a suitable cartridge installed, priming the system may include flushing cell release buffer from the flow path between valve 9204 through valve 9202 and up to the normally closed port of valve 9201 using pump 9103. Pump 9103 draws fluid from wash solution reservoir 9303 through valve 9204, valve 9202, valve 9201, valve 9203 and waste reservoir 9503. It is advantageous to conduct this priming step before priming the rest of the lines to allow subsequent priming steps to flush cell release solution completely out of the system and fill the lines with cell isolation solution instead. Valves 9200, 9201, 9203 and 9206 are unpowered. Pump 9101 and pump 9102 are powered, drawing fluid from the wash solution reservoir 9300 through valve 9206 and into the sample reservoir 9500 via straw 9501. Pump 9102 is stopped. Pump 9101 continues to pump, drawing fluid from wash solution reservoir 9300 through valve 9206, and into tubing cooling heat exchanger 9502, into prefilter 9402, valve 9200, valve 9201, cell capture column 9403, valve 9203 and waste reservoir 9503. Pump 9101 is stopped. Valves 9201, 9202, 9204 are powered. Valve 9203 is not powered. Pump 9103 draws fluid from wash solution reservoir 9303 through valve 9204, valve 9202, valve 9201, valve 9203 and waste reservoir 9503. In an exemplary embodiment, pump 9103 is capable of pumping at the cell release flow rate which is a higher flow rate than the cell capture flow rate as provided by pump 9102.

Analysis Cartridge Conditioning

After system priming, an exemplary method of detecting and monitoring includes installation of an unused analysis cartridge and includes pre-filter and capture column conditioning prior to loading a sample.

Installation of Analysis Cartridge

Prior to removal of sanitation/priming cartridge for installation of analysis cartridge, Valve 9207 is powered on to maintain system priming between valve 9207 and lysis filter 9404. Correct analysis cartridge is removed from overwrap and installed into correct, primed system bay and prompt system to verify correct cartridge. Once correct cartridge is installed, all valves are unpowered. Sample bag is installed and sample straw is attached. Before analysis, the system verifies bay temperature and ready status of all reagent solution reservoirs. If the system is not ready, appropriate message is relayed Conditioning In embodiments, the first half at low flow rate using pump 9101 is to condition prefilter and cell isolation filter. Valves 9200, 9201, 9203 and 9206 are unpowered. Pump 9101—is powered to flow 15 mL fluid at 10 mL/min from wash solution reservoir 9300 through pre-filter 9402 and cell isolation filter 9403 and flow-through is collected in waste reservoir 9503. Pump 9101 is stopped. Second step uses pump 9103 at approximately double or thrice flow rate through cell isolation filter only (excluding prefilter). In an exemplary embodiment, pump 9103 is capable of pumping at the cell release flow rate (which may be less or more than 30 mL/min) which is typically a higher flow rate than the cell capture flow rate as provided by pump 9102. In some embodiments, the second conditioning step of cell isolation filter 9403 flow rate is the same as the flow rate to be used for intended cell release. In some embodiments, the second conditioning step of cell isolation filter 9403, the liquid flowed is the same as is used for cell capture. In embodiments, flow rate for conditioning cell isolation filter and for cell release may be higher (for example, flow 15 mL fluid at 930 mL/min) than flow rate used for cell isolation. Valves 9201, 9202 and 9204 are powered. For conditioning the cell isolation filter 9403, pump 9204 (which may be peristaltic, syringe, diaphragm, or other) moves cell isolation solution from reservoir 9303 through valve 9201 and cell isolation filter 9403 through valve 9203 to waste reservoir 9503.

Sample Loading:

In an exemplary embodiment, after analysis cartridge installation the method includes loading the sample and capturing only the live cells. For example, a sample is loaded as a sample bag into sample loading chamber 9500. Sample straw 9501 is installed in valves 9200, 9201 and 9203 are unpowered. Pump 9101 is powered. The sample size for applications such as food pathogen analysis may be too large to practicably fit in a disposable cartridge. As such, an instrument must be sanitized after analysis of sample loaded from external sample reservoir.

In some examples, an air gap is created. In embodiments, an air gap is created to reduce and/or prevent mixing of buffer components because release performance deteriorates when buffers mix (e.g., release efficiency drops to less than 13% without a gap vs greater than 40% with approximately 3 mL air gap). Second, the air gap allows for efficient release of cells from the capture column as the air gap contributes "mechanically" to efficient release from the capture column. In embodiments, an air gap is created by a series of small gaps. In embodiments, the air gap is a contiguous air gap. In some examples, an air gap, such as a single air gap, of less than 5 mL is created, such as between 1 mL and 5 mL, between 2 mL to 4 mL, 3 mL to 5 mL, 1 mL to 3 mL, including about 1 mL, 2 mL, 3 mL, 4 mL, and 5 mL. It is contemplated that the air gap can be scalable with the dimensions (diameter and/or length) of the capture column. For example, in some embodiments, tubing diameter used within the system and method is about ⅛ inch in diameter and the introduced air gap is less than 5 mL, such as between 1 mL and 5 mL, between 2 mL to 4 mL, 3 mL to 5 mL, 1 mL to 3 mL, 2 mL to 3 mL, including about 1 mL, 2 mL, 3 mL, 4 mL, and 5 mL. In some embodiments, the air gap is sufficient to yield an release efficiency of greater than 10%, greater than 20%, greater than 30%, such as between 10% and 40%, 20% and 40%, 30% and 40%, 30% and 50% or more.

In an exemplary embodiment, the method includes exchanging buffer with lysis buffer and then removing the buffer.

In an exemplary embodiment, the method includes back flowing lysis buffer to release cells into removable PCR tube. Pump 9104 pulling air from the bubble trap 9504. Syringe pump 9104 is withdrawn, pulling lysis buffer from the lysis buffer reservoir 9303, such as pulling approximately 50 μL of lysis buffer from the lysis buffer reservoir 9303, through valve 9206 and 9205 into syringe pump 9104. Valves 9205 is powered and valves 9203, 9204 and 9207 are unpowered. The syringe pump 9104 is purged, pushing lysis buffer followed by air through valve 9204, through the top of the lysis filter 9404 and into the removable PCR tube 9503.

In some embodiments, the method includes the optional sanitation process. For the optional sanitation process, a sanitation cartridge is inserted and valves 9200, 9202 are powered. Pumps 9101 and 9102 are powered, drawing sanitation buffer from sanitation reservoir 9301 into and from the sample loading reservoir 9500, into tubing cooling heat exchanger 9501, pre-filter 9402, valve 9200, valve 9201, cell capture column 9403, valve 9203 and waste reservoir 9502.

The secondary structure of the aptamer is involved in binding the target because various folds allow the aptamer to exploit various binding mechanisms such as hydrophobicity, molecular shape complementarity, electrostatic, charge-dipole, or hydrogen bonding. The melting temperature (Tm) is defined as the temperature at which 50% of the complementary bases are hybridized in a double-stranded state and 50% of the bases are dissociated in single-stranded state. In order for target cells to specifically bind to aptamers, the temperature of the assay is to be below the melting temperature to ensure properly formed, stable aptamer structures. Numerous factors affect the melting temperature of a nucleic acid strand including the length and GC content of the strand, monovalent ions (sodium, potassium, Tris), magnesium ions and commonly used denaturing agents such as formamide and DMSO.

Aptamer selection is typically accomplished using a technique called Systematic Evolution of Ligands by Exponential Enrichment (SELEX). Target-specific sequences are obtained by the cycles of selection and replication. The library containing sequences with a particular length is incubated with target molecules. This incubation leads to binding of aptamers with the highest affinity with the target molecule. During the process, only nucleic acids bound with target compound are selected and undergo replication, while the other nucleotides are removed from the sequence library. Specific aptamers can be generated for molecules, bacteria, viruses, and cells. The SELEX process is usually performed at room temperature using a 1×PBS (phosphate buffered saline) buffer such as one containing 137 mM NaCl, 2.7 mM KCl, 8.1 mM Na2HPO4, 1.76mMKH2PO4. It is contemplated that other buffers can be used, such as Tris-HCl, comprised of 50 mM Tris, 150 mM NaCl, 5 mM MgCl2, 1 mM EDTA. The buffer composition is selected to ensure proper aptamer hybridization, which typically results in the equivalent of roughly 160 mM of monovalent cations. In some embodiments, the buffer used to bind cells is the same as that used in the SELEX process in order to maximize specific binding. For example, all aptamer processes are performed in a 1×PBS buffer or a Tris-HCl buffer as detailed above.

The inventors have discovered that by changing the buffer solution, aptamer binding can be biased to favor live bacteria cells over dead ones. For example, in one embodiment, the method utilizes 0.2×PBS, then adds 2 mM magnesium to the buffer, and reduces the temperature to 11 degrees Celsius. These conditions facilitate aptamers binding live cells, but not dead cells. Detection of dead cells would be considered a false positive. In some embodiments, less than 1% of cells detected are dead, such as between 1% and 0.5%, 0.5%, 0.1%, 0.01% and 0%, including 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01% of the cells detected are dead.

In one specific embodiment, the system utilizes sample processing, targeted aptamer cell capture, rRNA extraction and RT-PCR or isothermal amplification to meet industry needs including sample size, sample collection methods, live cell analysis, sensitivity, and specificity.

In other embodiments, cell isolation is accomplished by antibody/antigen cell capture.

The disclosed system and method enable multiplexed analysis of bacterial, viral, and fungal cells in numerous media including, but not limited to, food industry samples, drinking water, waste material, industrial liquids, soil samples, aquatic biome samples and clinical and veterinarian samples which may include blood, sputum, stool, gut and organs. Isolation of target cells from complex matrices such as environmental samples from the food industry can be challenging. Filtering cannot effectively isolate small quantities of target cells in many non-clinical sample matrices. Particles that are essentially the same size as target cells, such as clay, along with numerous non-target cells can overwhelm a filter. In addition, size-based isolation lacks the specificity required to ensure a given nucleic acid amplification region is unique to the target organism. In many applications the sample volume can vary greatly. What is desirable is a new method to isolate target cells from samples of various volumes in the presence of large numbers of non-target cells and other substances of similar size. The disclosed system is designed to maximize the capture efficiency of target cells by flowing the sample through a tortuous path of target cell binding surfaces. This allows small, undesired particles in the sample to pass through unimpeded and maximizes the opportunity for target cells to bind to a surface. It also allows rapid capture of small quantities of cells in large samples and can be performed inexpensively without human intervention. In embodiments, the disclosed system uses a capture column which is different than aptamer affinity purification used to isolate target bacteria. The application of aptamer affinity purification was first reported in 1999 for an L-selectin-immunoglobulin fusion protein (Romig et al., J. Chromatogr. B. 1999; 731 (2):275-284). The disclosed system uses a capture column containing glass beads roughly 100 μm in diameter. Some of the advantages of the disclosed approach include removal of inhibitors to the amplification process by washing the cells in the column, release of the cells, and further cell concentration using a filter to reduce the liquid volume to 20-50 uL. In addition, the disclosed system and method in embodiments adds a filtration column, prior to the capture column, containing beads of similar size as the capture column to remove large particles from the sample. Although the concept of using small particles, such as SiO2, as a filter, dates back to at least the 3rd or 4th century in India, when the Sushruta Samhita recommended filtering water through sand and coarse gravel, the disclosed system is dramatically different. Previous systems were used for water purification and therefore designed to block the passage of all particles, including bacteria cells. The disclosed system is designed to allow the passage of specific substances, such as bacteria. It uses the unique combination of beads in filter column followed by beads capture column where the beads in the filter column contain similar or smaller size than the beads in the capture column. It should be noted that both the filter column and the capture column can contain multiple size beads. In some embodiments, the smallest beads in the filter column are the same size or smaller than capture beads in the capture column. The filter column beads have non-fouling surface chemistry. In some embodiments, the disclosed system utilizes similar or the same surface chemistry on the filter beads as the capture column beads. In some embodiments, the disclosed system and method allows the filter column to be bypassed to enable effective washing and release of cells in capture column. In some embodiments, the disclosed system includes a filter column that is funnel shaped to maximize filtering load capacity of very large particles at the input and provide a long filter path to capture smaller particles. In food safety testing, a filter blender bag is often used, such as the Nasco Whirl-Pak B01385 W having a large membrane filter with pore size of 330 microns. The filter column is then used to filter out particles that are smaller than 330 μm but large enough so as not to pass in the gaps between the 100 μm beads in the capture column. The beads in filter column must be no larger than the beads in the filter column to be assured that any substance that passes through the filter column can pass through the capture column.

The disclosed flow-through process captures foodborne pathogens with aptamers, such as DNA aptamers or antibodies. For example, the system contains a highly efficient process to rapidly isolate, wash, release and concentrate cells, extract the ribosomal RNA (rRNA) and deliver an inhibitor-free sample volume of ~40 μL for nucleic acid amplification analysis without the need to purify the RNA after extraction. Most nucleic acid amplification processes rely on purification after nucleic acid extraction to remove inhibitors. Nucleic acid purification results in loss of specificity due to dilution and/or losses in the purification process. The disclosed system is designed to detect a small number of cells and very few nucleic acid copies. The disclosed system purifies the assay at the cell level to eliminate the need for nucleic acid purification.

To minimize transfer losses, in some embodiments, the disclosed system and method extract the nucleic acids from cells in the same container as used for nucleic acid amplification. The chamber is sealed prior to loading the cells so the amplification reagents and lysis beads are not lost during transport and the chamber is sealed again prior to nucleic acid amplification to minimize or avoid losses from spillage when the container is transferred to the amplification device and during nucleic acid amplification to minimize or avoid losses from evaporation. In some examples, in order to introduce the cells into the chamber, the disclosed system uses a non-coring needle in a septum with an optional second non-coring needle for air to relieve pressure as the liquid is introduced into the chamber.

In some embodiments, the disclosed system and method perform nucleic acid extraction with mechanical lysis performed using sonication using beads, preferably made with yttrium-stabilized zirconia. Yttrium-stabilized zirconia is very hard, has a high density of roughly 6 g/cm3. Nucleic acid amplification is typically performed with liquid volumes of 20 uL to 40 uL. Larger volumes can be used but at an increased cost for the reagents. To excite the beads, the disclosed system and method uses an ultrasonic transducer with a mechanical connection to the chamber.

In some embodiments, the method and system allows for aptamer/epitope combinations associated with live cell binding versus dead cell binding to be determine. In some examples, the method and system accounts for live cell capture versus dead cell capture in the aptamer selection process. For example, the disclosed method and system utilize the disclosed buffer conditions in the SELEX process with both live cells and dead cells to find the desired aptamer/epitope combinations. In other examples, the disclosed method and system use two or more different buffer conditions in the SELEX process. It is contemplated that other processes can be used for aptamer selection.

In some embodiments, a system and method to automatically link a machine-readable code on a sample collection bag from a food industry sample to sample analysis results is provided. In some embodiments, a machine-readable code is an optical barcode. In some embodiments, the method includes a machine-readable code on a sample collection bag; a machine-readable code on a bag used for paddle blending a sample; a machine-readable code on a cartridge used for sample analysis; a method to determine sample analysis results; and a database to automatically link the machine-readable code on the sample collection bag to the sample analysis. In some embodiments, the sample collection bag and the bag used for paddle blending the sample are the same bag. In some embodiments, a machine-readable code on a sample collection bag can be associated to one or more of the sample collection location, sample collection time, sample type, and other sample specifics. In some embodiments, the machine-readable code on the cartridge can be associated with the type of analysis for that cartridge and one or more of the cartridge type, unique identifier, manufacturing data such as the date and location, and the expiration date. In some embodiments, specific cartridge details, such as usage data viability for analysis can be obtained from a database. In some embodiments, this information confirms whether the selected cartridge can process the desired sample. In some embodiments, the machine-readable code on the cartridge is electronic and can be read and written by multiple devices such as the diagnostic cartridge analysis system.

In some embodiments, the database to link the machine-readable code on the sample collection bag resides on a local computer or on a server accessible from a computer network. In some embodiments, sample collection information is linked to the machine-readable code on a cartridge. In some embodiments, sample collection information is linked to the machine-readable code on the cartridge to confirm the cartridge is capable of performing an analysis comprising determining type of pathogens or infectious agents the cartridge has been configured to analyze; and determining viability of the cartridge, such as the age and whether the cartridge has been previously used. In some embodiments, the food industry sample is one or more of a food product or a food processing environmental sample. In some embodiments, the food industry sample is paddle blending with more than 25 milliliters of an aqueous solution prior to analysis.

In some embodiments, a straw is placed in the sample collection bag and the sample is removed from the sample collection bag with negative pressure, such as with a peristaltic pump. The pump withdraws the sample from the bag. In some embodiments, a liquid level sensor senses when the end of liquid is detected. In some embodiments, the sample collection bag contains a filter to remove large particulates. In some examples the volume of liquid withdrawn from the bag can be determined based on factors such as the flow rate and the time. In some embodiments, the amount of liquid withdrawn from the bag can be used to determine whether a sufficient volume of liquid was withdrawn from the bag.

In some embodiments, pathogen isolation occurs at a temperature below or above the sample temperature, such as between 9 °C and 12 °C in order to isolate only live cells. In some embodiments, the sample is applied to a tubing heat exchanger to cool or heat the sample temperature prior to pathogen isolation. In some embodiments, the heat exchanger contains a one or more flow paths having thermal conductive properties, such as stainless steel, in which the sample passing through the tubes is cooled or heated to the surrounding temperature. In some embodiments, the heat exchanger is heated or cooled by a thermally connected device, such as a thermoelectric device. In some embodiments, the heat exchanger is inside in a thermally insulated air or liquid container and the temperature inside the container is heated or cooled by a refrigeration or heating system. In some examples, the system includes one or more thermostats to achieve and maintain the desired operating temperature. In some examples, the system is operated in a temperature controlled environment. In some embodiments, the heat exchanger has sufficient thermal capacity to equilibrate the sample volume at the capture flow rate to within the specified temperature range to capture only live cells.

IV. Exemplary Computer Environments i. Example Cloud Computing Environment

Figure 10:
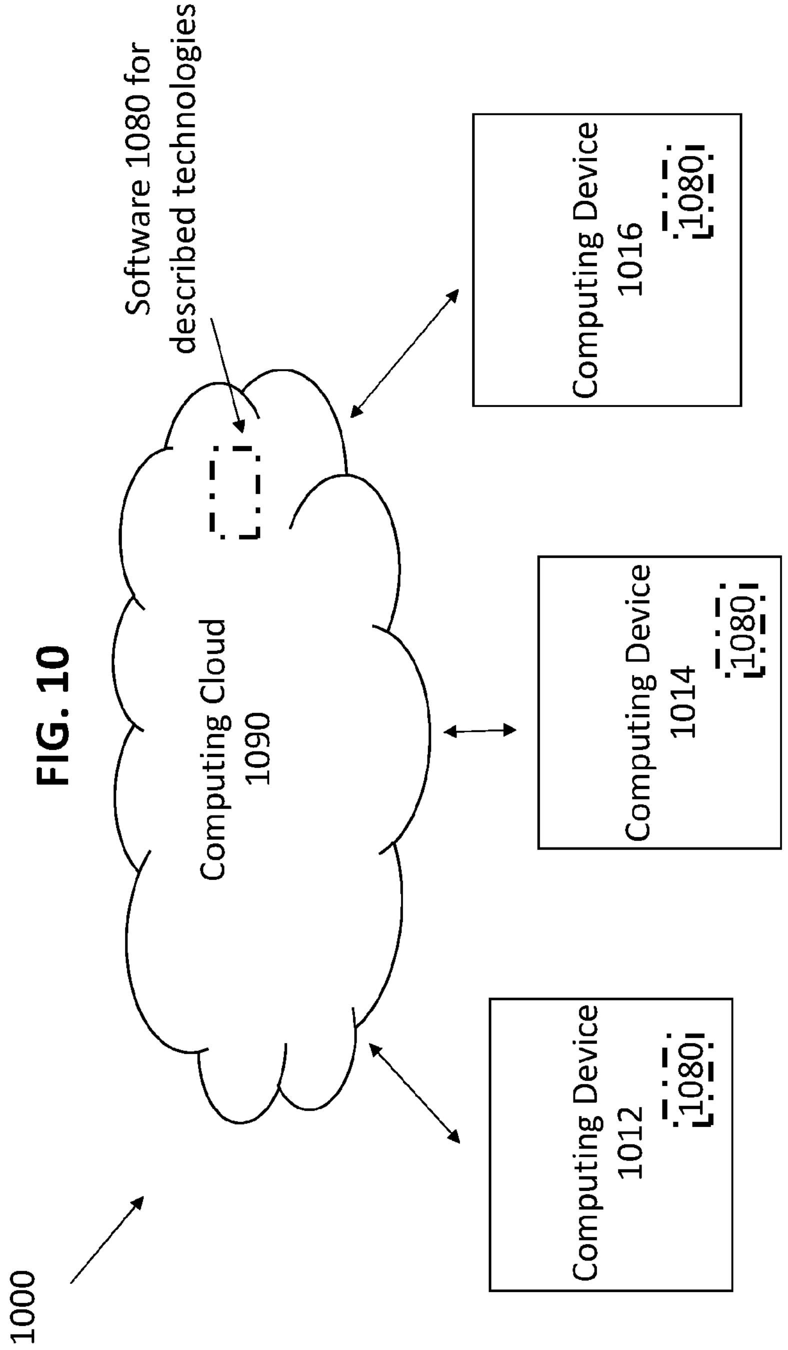
FIG. 10 depicts an example cloud computing environment 1000 in which the described technologies can be implemented.

FIG. 10 depicts an example cloud computing environment 1000 in which the described technologies can be implemented. The cloud computing environment 1000 comprises a computing cloud 1090 containing resources and providing services. The computing cloud 1090 can comprise various types of cloud computing resources, such as computer servers, data storage repositories, networking resources, and so forth. The computing cloud 1090 can be centrally located (e.g., provided by a data center of a business or organization) or distributed (e.g., provided by various computing resources located at different locations, such as different data centers, laboratories, institutions and/or located in different cities or countries).

The computing cloud 1090 can be operatively connected to various types of computing devices, such as computing devices 1012, 1014, and 1016, and can provide a range of computing services thereto. One or more of computing devices 1012, 1014, and 1016 can be computers (e.g., server, virtual machine, embedded systems, desktop, or laptop computers), mobile devices (e.g., tablet computers, smartphones, or wearable appliances), or other types of computing devices. Connections between computing cloud 1090 and computing devices 1012, 1014, and 1016 can be over wired, wireless, or optical links, or any combination thereof, and can be short-lived or long-lasting. These connections can be stationary or can move over time, being implemented over varying paths and having varying attachment points at each end. Computing devices 1012, 1014, and 1016 can also be connected to each other.

Computing devices 1012, 1014, and 1016 can utilize the computing cloud 1090 to obtain computing services and perform computing operations (e.g., data processing, data storage, and the like). Particularly, software 1080 for performing the described innovative technologies can be resident or executed in the computing cloud 1090, in computing devices 1012, 1014, and 1016, or in a distributed combination of cloud and computing devices.

ii. Generalized Computer Environment

Figure 11:
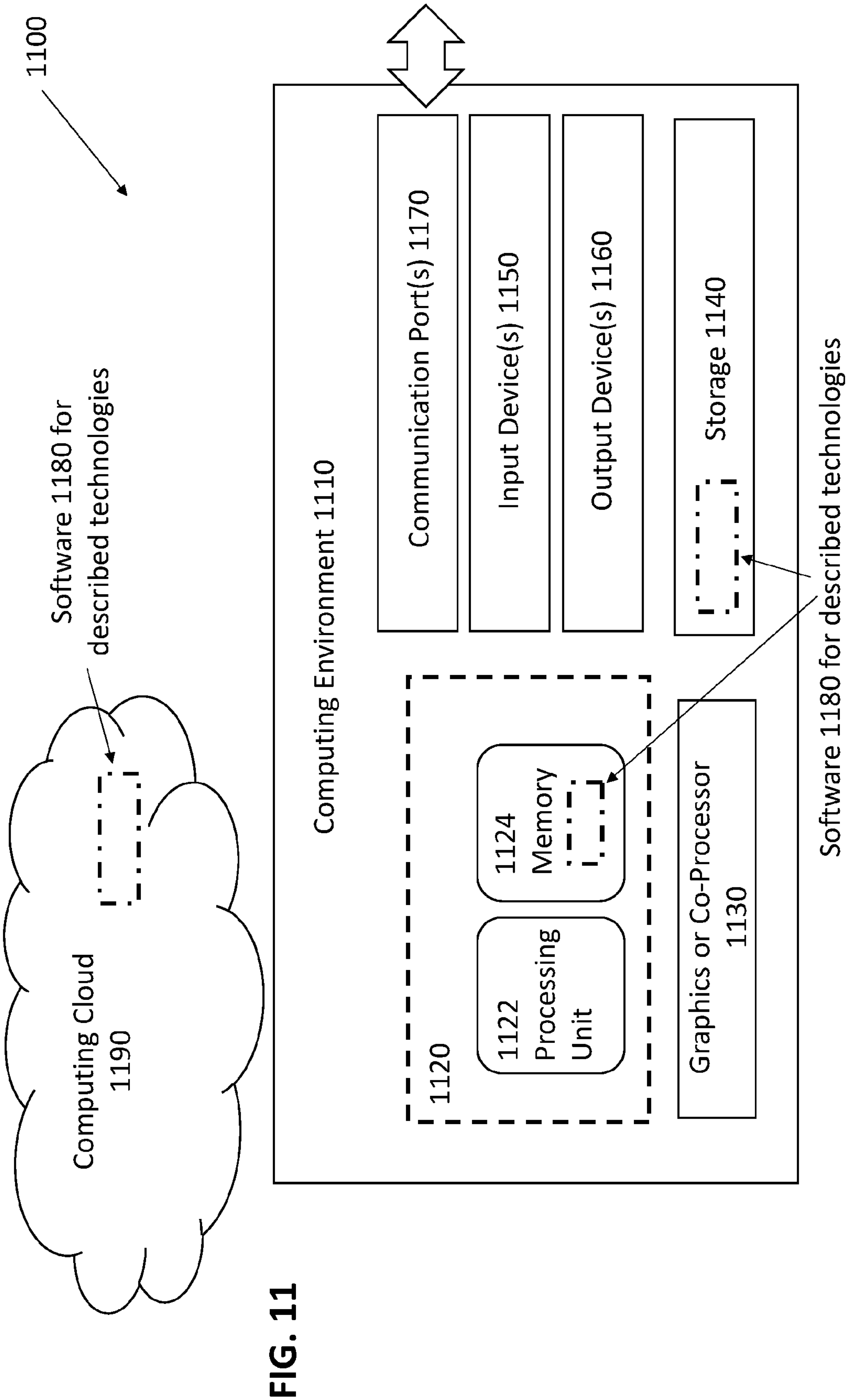
FIG. 11 illustrates a generalized example of a suitable computing system 1100 in which described examples, techniques, and technologies, including construction, deployment, operation, and maintenance of a disclosed system.

FIG. 11 illustrates a generalized example of a suitable computing system 1100 in which described examples, techniques, and technologies, including construction, deployment, operation, and maintenance of a disclosed system can be implemented according to disclosed technologies. The computing system 1100 is not intended to suggest any limitation as to scope of use or functionality of the present disclosure, as the innovations can be implemented in diverse general-purpose or special-purpose computing systems.

With reference to FIG. 11, computing environment 1110 includes one or more processing units 1122 and memory 1124. In FIG. 11, this basic configuration 1120 is included within a dashed line. Processing unit 1122 executes computer-executable instructions, such as for implementing any of the methods or objects described herein for identifying, monitoring and quantitating pathogens described herein. Processing unit 1122 can be a general-purpose central processing unit (CPU), a processor in an application-specific integrated circuit (ASIC), or any other type of processor. In a multi-processing system, multiple processing units execute computer-executable instructions to increase processing power. Computing environment 1110 can also include a graphics processing unit or co-processing unit 1130. Tangible memory 1124 can be volatile memory (e.g., registers, cache, or RAM), non-volatile memory (e.g., ROM, EEPROM, or flash memory), or some combination thereof, accessible by processing units 1122, 1130. The memory 1124 stores software 1180 implementing one or more innovations described herein, in the form of computer-executable instructions suitable for execution by the processing unit(s) 1122, 1130. The memory 1124 can also store configuration data, tree structure information, tables including structure tables, data tables, working tables, change logs, output structures, input vectors, output vectors, indices, or flags, as well as other configuration and operational data.

A computing system 1110 can have additional features, such as one or more of storage 1140, input devices 1150, output devices 1160, or communication ports 1170. An interconnection mechanism (not shown) such as a bus, controller, or network interconnects the components of the computing environment 1110. Typically, operating system software (not shown) provides an operating environment for other software executing in the computing environment 1110, and coordinates activities of the components of the computing environment 1110.

The tangible storage 1140 can be removable or non-removable, and includes magnetic disks, magnetic tapes or cassettes, CD-ROMs, DVDs, or any other medium which can be used to store information in a non-transitory way and which can be accessed within the computing environment 1110. The storage 1140 stores instructions of the software 1180 (including instructions and/or data) implementing one or more innovations described herein.

The input device(s) 1150 can be a mechanical, touch-sensing, or proximity-sensing input device such as a keyboard, mouse, pen, touchscreen, trackball, a voice input device, a scanning device, or another device that provides input to the computing environment 1110. The output device(s) 1160 can be a display, printer, speaker, optical disk writer, or another device that provides output from the computing environment 1110.

The communication port(s) 1170 enable communication over a communication medium to another computing device. The communication medium conveys information such as computer-executable instructions or other data in a modulated data signal. A modulated data signal is a signal that has one or more of its characteristics set or changed in such a manner as to encode information in the signal. By way of example, and not limitation, communication media can use an electrical, optical, RF, acoustic, or other carrier.

In some examples, computer system 1100 can also include a computing cloud 1190 in which instructions implementing all or a portion of the disclosed technology are executed. Any combination of memory 1124, storage 1140, and computing cloud 1190 can be used to store software instructions and data of the disclosed technologies.

The present innovations can be described in the general context of computer-executable instructions, such as those included in program modules, being executed in a computing system on a target real or virtual processor. Generally, program modules or components include routines, programs, libraries, software objects, classes, components, data structures, etc. that perform tasks or implement particular abstract data types. The functionality of the program modules can be combined or split between program modules as desired in various embodiments. Computer-executable instructions for program modules can be executed within a local or distributed computing system.

The terms "system," "environment," and "device" are used interchangeably herein. Unless the context clearly indicates otherwise, none of these terms implies any limitation on a type of computing system, computing environment, or computing device. In general, a computing system, computing environment, or computing device can be local or distributed, and can include any combination of special-purpose hardware and/or general-purpose hardware and/or virtualized hardware, together with software implementing the functionality described herein. Virtual processors, virtual hardware, and virtualized devices are ultimately embodied in a hardware processor or another form of physical computer hardware.

In some specific embodiments, a smartphone, tablet, laptop computer or other computing devices have the capability to scan or enter barcode information linked to a sample collection bag. In some embodiments, the barcode can be scanned optically or electronically. In some embodiments, the computing device transmits the barcode data to a sample collection database including metadata related to sample and/or sample collection, such as the sample collection location, sample collection time, sample type, and environmental conditions.

In some embodiments, the sample is further processed after collection, such as with a paddle blender, and a computing device transmits the barcode data on a sample collection bag to the sample database including data related to sample processing.

In some embodiments, cartridge data related to the manufacture of a cartridge having a machine-readable code is provided to a cartridge database. In some embodiments, the cartridge data can be associated with which pathogens and the type of sample the cartridge is capable of analyzing. In some embodiments, the cartridge data can be associated with one or more of the cartridge manufacturing information, cartridge storage information, cartridge viability, or cartridge lifetime. In some embodiments, the cartridge data can be associated with data related to the number of type of prior cartridge uses.

In some embodiments, the sample collection database and the cartridge database are compared prior to analyzing a sample. In some embodiments, analysis parameters may be changed or analysis may be prevented after the sample collection database and the cartridge database are compared. In some embodiments, the sample is analyzed and analysis data is provided. In some embodiments, analysis data is uploaded to an analysis database. In some embodiments, the analysis database is linked and compared to the sample collection database and the cartridge database.

In some embodiments, the analysis data is represented graphically. In some embodiments, the graphical representation of analysis data, contains a coordinate axis wherein a first and second axis of each data point can be correlated to a location where samples are collected, such as where food is processed, prepared, stored, distributed, sold and/or consumed. In some embodiments, a first and second axis of each data point can be correlated to a location where people are present, such as in locations where people congregate or work. In some embodiments, a first and second axis of each data point can be correlated to one location of a farm, field or where animals are present. In some embodiments, the number of one or more pathogens at each location is represented by a third axis such as the z axis on an xyz coordinate plot. In some embodiments, the number of one or more pathogens at each location is represented by one or more differences in color, hue or intensity, such as in a color or grayscale heat map. In some embodiments, the number of one or more pathogens at each location is represented by a continuous representation of data such as data that is interpolated, curve fit and/or estimated. In some embodiments, the number of one or more pathogens at each location is represented by values on the graphical representation of analysis data. In some embodiments, the number of one or more pathogens at each location includes historic data.

GENERAL CONSIDERATIONS

Although the operations of some of the disclosed methods are described in a particular, sequential order for convenient presentation, it should be understood that this manner of description encompasses rearrangement, unless a particular ordering is required by specific language set forth below. For example, operations described sequentially can in some cases be rearranged or performed concurrently. Moreover, for the sake of simplicity, the attached figures may not show the various ways in which the disclosed things and methods can be used in conjunction with other things and methods.

Theories of operation, scientific principles, or other theoretical descriptions presented herein in reference to the system or methods of this disclosure have been provided for the purposes of better understanding and are not intended to be limiting in scope. The system and methods in the appended claims are not limited to those apparatus and methods that function in the manner described by such theories of operation.

Any of the disclosed methods can be implemented as computer-executable instructions or a computer program product stored on one or more computer-readable storage media, such as tangible, non-transitory computer-readable storage media, and executed on a computing device (e.g., any available computing device, including tablets, smartphones, or other mobile devices that include computing hardware). Tangible computer-readable storage media are any available tangible media that can be accessed within a computing environment (e.g., one or more optical media discs such as DVD or CD, volatile memory components (such as DRAM or SRAM), or nonvolatile memory components (such as flash memory or hard drives)). By way of example, and with reference to FIG. 11, computer-readable storage media include memory 1124, and storage 1140. The term computer-readable storage media does not include signals and carrier waves. In addition, the term computer-readable storage media does not include communication ports (e.g., 1170) or communication media.

Any of the computer-executable instructions for implementing the disclosed techniques as well as any data created and used during implementation of the disclosed embodiments can be stored on one or more computer-readable storage media. The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network, a cloud computing network, or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in ABAP, Adobe Flash, C, C++, C#, Curl, Dart, Fortran, Java, JavaScript, Julia, Lisp, Matlab, Octave, Perl, Python, R, Ruby, SAS, SPSS, SQL, WebAssembly, any derivatives thereof, or any other suitable programming language, or, in some examples, markup languages such as HTML or XML, or in any combination of suitable languages, libraries, and packages. Likewise, the disclosed technology is not limited to any particular computer or type of hardware. Certain details of suitable computers and hardware are well known and need not be set forth in detail in this disclosure.

Furthermore, any of the software-based embodiments (comprising, for example, computer-executable instructions for causing a computer to perform any of the disclosed methods) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, infrared, and optical communications), electronic communications, or other such communication means.

The disclosed methods and systems should not be construed as limiting in any way. Instead, the present disclosure is directed toward all novel and nonobvious features and aspects of the various disclosed embodiments, alone and in various combinations and sub-combinations with one another. The disclosed methods and systems are not limited to any specific aspect or feature or combination thereof, nor do the disclosed embodiments require that any one or more specific advantages be present or problems be solved. The technologies from any example can be combined with the technologies described in any one or more of the other examples. The disclosure is further illustrated by the following non-limiting Examples.

EXAMPLES

Example 1

Development of an Integrated Detection Platform for the in-Process Surveillance of *Listeria* Spp. in Environmental Monitoring Samples This example demonstrates the ability to detect *Listeria* in food industry environmental samples taken from produce/leafy green processing facilities with the disclosed system and method.

*Listeria monocytogenes* is a significant cause of foodborne illness. In the general population, most cases are expressed as a mild illness, but susceptible populations of pregnant women, neonates, elderly, or immune-compromised humans have a much higher incidence of systemic (invasive) listeriosis resulting in abortion, stillbirth, septicemia, meningitis and meningoencephalitis, with a mortality rate of about 30%. The annual economic impact of listeriosis in the United States is estimated at over $2.8 billion.

*L. monocytogenes* is widespread in the environment, and control of *Listeria* in food production facilities requires constant focus by risk managers. Conventional culture-based methods rely on detecting a single bacterium through growth of a single cell into a colony, a process that can take several days. The time to culture can vary based on many factors. It has been found that some stressed cells can take many days to culture. It has also been shown that cells can be viable but nonculturable (see, for example, ncbi.nlm.nih.gov/pubmed/29666286 on the world wide web). Culturing also effectively dilutes many PCR inhibitors. Eliminating the need for culturing prior to analysis will greatly reduce total-time-to-results and enable effective intervention strategies to reduce and mitigate the presence of *Listeria*. Thus, the objective of this study was to develop and validate an integrated detection platform for the in-process surveillance of foodborne pathogens.

To achieve a high level of sensitivity in environmental samples, the method targeted conserved high copy sequences in the ribosomal RNA of *Listeria* spp. As illustrated in FIG. 1, Bacterial cells were subjected to a flow through aptamer-capture step and rinsed, followed by sample concentration and mechanical lysis. RNA copies were either purified or recovered from crude lysate and were further reverse transcribed. The amplification by reverse transcriptase-qPCR of the ribosomal RNA targeted region was achieved using modified nucleotides to stabilize DNA duplex and promote higher specificity. FIGS. 2-7 show the results of the aforementioned studies. In particular, validation experiments indicated that the probe-based assay had an RNA analytical sensitivity limit of less than 10 fg of *Listeria* RNA or less than 5 CFU/ml by using crude lysate as template (Fisher's exact test, $p<0.0001$). No positive signals were detected when testing non-targeted environmental bacterial strains, such as *Bacillus* spp., *Citrobacter* spp. *Enterobacter* spp., and *Pseudomonas* spp., and observations indicated low concentrations of *Listeria* were still detected in the presence of 1000 times the amount of non-target RNA. The feasibility of detecting *Listeria* spp. from sponge-swab samples, collected at a leafy greens processing facility, was evaluated. Results showed that *Listeria* spp. were detected at concentrations ranging from 3 CFU/ml to 32 CFU/ml (Fisher's exact test, $p<0.001$), recovered from spiked 100 ml-volume samples in the absence of an enrichment culturing step. These data have set the foundation for developing an integrated system to rapidly detect *Listeria* at low cell concentrations from environmental samples in large volume amounts without enrichment steps.

REFERENCES (EACH OF WHICH IS HEREBY INCORPORATED BY REFERENCE IN ITS ENTIRETY)

Livezey, K et al., A new generation of food-borne pathogen detection based on ribosomal RNA. Annu. Rev. Food Sci. Technol. 2013. 4:313-25.

Milner, M. G., et al. (2001). Relationship between nucleic acid ratios and growth in *Listeria monocytogenes*. Microbiology. 2001 147: 2689-2696.

Reddington K, et al. A current overview of commercially available nucleic acid diagnostics approaches to detect and identify human gastroenteritis pathogens. 2014. Biomol Detect Quantif 1:3-7.

Suh S H, Jaykus L A. Nucleic acid aptamers for capture and detection of *Listeria* spp. J Biotechnol. 2013. 167:454-461.

Teng J, et al. Aptamer-based technologies in foodborne pathogen detection. 2016. Front Microbiol 7:1426.

Example 2

Materials and Methods

I. Equipment
- Optical microscope
- Neubauer Hemocytometer
- Hot water bath or hotplate
- Thermometer
- Magnetic stirrer hot plate, such as Thermolyne Nuova stir/heat plate, or similar
- Environmental chamber, such as a Tenney Junior model TLJR temperature control chamber
- Peristaltic pump, such as a Masterflex model 7550-60
- Benchtop microcentrifuge such as Eppendorf model 5415C or 5415D or similar
- Vortex mixer, such as a benchtop VWR Mini Vortex, VWR Scientific Vortex-Genie 2, or similar, set to setting 7

II. Materials

*Listeria* culture, fresh, grown in appropriate growth media, such as prepared by inoculating a 10 mL tube of brain heart infusion (BHI) broth, such as Hardy Diagnostics BHI Broth part no. K25, and grown in a warm environment (~25-37 °C) overnight (>12 hours).

500 mL of capture buffer (0.2×PBS, 2 mM MgCl2, 0.2% Triton X-100) such as prepared by combining 470 mL high purity water, 10 mL of 10×PBS solution, pH 7.4 (such as Teknova 10×PBS solution, pH 7.4, CAT No. P0916), 10 mL of 100 mM MgCl2 (such as prepared using Sigma magnesium chloride hexahydrate, Sigma Ultra Cat. No., M-2670), 10 mL of 10% v/v Triton X-100 solution (such as prepared using EMD Triton X-100, Cat. No. TX1568-1, diluted by volume, and thoroughly dissolved in high purity water, such as with a glass beaker with stir magnet and stirred well using a stir plate, such as Thermolyne Nuova stir/heat plate, or similar, on gentle setting until well mixed) 100 mL of release buffer (1M NaCl, 100 mM EDTA, 0.1% Tween 20, 0.05% SDS, 30 mM $NaHCO_3$, pH 10.3-10.4) such as prepared by mixing approximately 20 mL high purity water, 20 mL of 500 mM EDTA pH 8 (such as Sigma-Aldrich Cat. No. 431788 or similar, dissolved in high purity water and titrated to pH 8 using 5M NaOH (such as a Fisher Scientific NaOH, Cat No S318, or similar dissolved in high purity water), 33 mL of 3M NaCl (such as prepared using Sigma-Aldrich Cat No. S7653, or similar), 3 mL of 1M $NaHCO_3$ pH 10.3 (such as prepared by dissolving $NaHCO_3$, Sigma-Aldrich Cat. No. S697, or similar, in high purity water and titrating to pH 10.3 using 5M NaOH, such as a Fisher Scientific NaOH, Cat No S318, or similar, dissolved in high purity water), 1 mL of 10% v/v Tween 20 (such as prepared by dissolving Tween 20, Sigma-Aldrich Cat No. P1379 or similar, in high purity water), 5 mL of 1% m/v SDS (such as prepared using Sigma Cat No. L3771, or similar, dissolved in high purity water), and pH adjusted to 10.3 using 5M NaOH (such as a Fisher Scientific NaOH, Cat No S318, or similar dissolved in high purity water), and brought to final total volume of 100 mL with high purity water.

100 mL of lysis buffer (0.1% Tween 20, such as prepared by diluting Tween 20, Sigma-Aldrich Cat No. P1379 or similar, in high purity water).

Trypan Blue dye, such as Sigma T8154, or similar.

Capture beads: 100 μm glass beads (such as BioSpec soda lime beads Cat. No. 11079101 or similar) such as prepared with surface modification for silane attachment, such as described in gelest.com/wp-content/uploads/Goods-PDF-brochures-couplingagents.pdf, which is hereby incorporated by reference as available on Jul. 23, 2019, and DNA aptamers attached using a process such as described in sfvideo.blob.core.windows.net/sitefinity/docs/default-source/technical-report/attaching-oligos-to-solid-supports.pdf?sfvrsn=47483407_6, which is hereby incorporated by reference as available on Jul. 23, 2019, with the surface blocked using a blocking agent such as arrayit.com/Products/Microarray_Buffers/Blocking_Solutions/Blocklt-_Blocking_Buffer/blockit_blocking_buffer.html, which is hereby incorporated by reference as available on Jul. 23, 2019.

Prefilter beads: 100 μm glass beads (such as BioSpec soda lime beads Cat. No. 11079101 or similar) such as prepared with the surface blocked using a blocking agent such as arrayit.com/Products/Microarray_Buffers/Blocking_Solutions/Blocklt_Blocking_Buffer/blockit_blocking_buffer-.html, which is hereby incorporated by reference as available on Jul. 23, 2019, or similar.

Lysis filter, such as assembled using a supported filter holder such as Millipore Swinnex, Cat. No. SX0001300, or similar, and a wettable 0.2 μm pore size filter membrane such as a polycarbonate, cellulose, PES, or similar, such as Sterlitech Polycarbonate Membrane Filters, Cat. No. PCT0213100, or similar.

50 mL conical tubes (such as Corning, VWR, Becton Dickinson).

Microcentrifuge tubes, such as Eppendorf LoBind, Cat. No. 022431048 or similar.

PCR tubes and caps, such as Molecular Bioproducts, Cat. No. 3418, or similar.

Lysis buffer with composition 0.1% v/v Tween 20, such as prepared by dissolving Tween 20, Sigma-Aldrich Cat No. P1379 or similar, in high purity water).

Live cell suspension sample in buffer. Samples for analysis were prepared using overnight cell suspension, the concentration of which was determined using hemocytometer and optical counts of diluted cells prepared as follows. Cells were washed by transferring 1-2 mL aliquots of the overnight cell suspension to 2 mL microfuge tubes (Eppendorf LoBind, Cat. No. 022431048, or similar) and centrifuging (using a benchtop microcentrifuge such as Eppendorf model 5415C or 5415D or similar) set for 2-10 minutes at >12000 rpm to pellet cells, discarding the supernatant and resuspending the cell pellet(s) to their original volume in capture buffer or in ~0.2× to 1×PBS (prepared by diluting 10×PBS (such as Teknova 10×PBS solution, pH 7.4, Cat. No. P0916, or similar) volumetrically in high purity water. Resuspension of cells was achieved by vortexing using a benchtop VWR Mini Vortexer, VWR Scientific Vortex-Genie 2, or similar, set to setting 7 (or a setting sufficient to completely resuspend the pellet after ~30 seconds). Cell suspensions were washed a second time following the same procedure as above.

Environmental sample in sample buffer, such as a filtered stomached sample is generated by stomaching an environmental sponge sample (such as generated using a 3M Sponge Stick, Cat. No. SSL10NB, or similar) in 90 mL of sample buffer in a 300 μm filtered stomaching bag (such as Whirl-Pak, B01547WA, or similar) for 3 minutes (either manually or by using an automated Stomacher, such as Seward stomacher, or similar).

One or more capture columns containing capture beads, such as prepared using a 3/16 inch ID inert or 1/8 inch ID inert tubing, such as Versilon™ Inert Tubing SE-200, of sufficient length, such that the resulting bead bed is retained with one or more mechanisms to prevent bead loss, such as using stainless steel frits inserted at one or more ends of the capture column.

One or more prefilters, such as a leak-free container comprised of an inert material such as polypropylene, with an inlet port connector to a funnel-shaped opening and an outlet port connected to a 10-40 mm long, 1/8" ID tube, such container containing prefilter beads, with a mechanism to prevent bead loss such as using stainless steel frits inserted at the output port.

Zirconia beads, such as BioSpec Zirconia beads, Cat. No. 11079110zx, or similar.

Biocompatible peristaltic pump tubing such as Saint-Gobain PharMed® BPT part #:AY242002.

Biocompatible system tubing, such as Versilon™ Inert Tubing SE-200, or similar.

A tubing heat exchanger such as tubing submerged in a water bath.

Ultrasonic transducer such as Tide Wand, or similar.

PCR instrument, such as Applied Biosystems 7500 or similar.

Example 3

Live Cell Capture Analysis

I. Condition the System

A capture column was placed in an environmental chamber at approximately 10 °C to 12 °C. The system was conditioned by flowing approximately 30 mL of capture buffer through the capture column at 15 ml/min using peristaltic pump and discarding the flow-through buffer.

II. Live Cell Capture Analysis

A 10 mL live cell reference buffer was created using cells diluted in capture buffer, and a 5 μL reference count aliquot was taken from the 10 mL sample. A second 5 μL aliquot was taken for trypan blue testing to confirm all cells were live. An air gap was introduced to the capture column before the live cell reference buffer sample to prevent dilution from the conditioning buffer, and an air gap was introduced after the sample to ensure entire 10 mL live cell reference was collected. The 10 mL sample was flowed through capture column and the flowthrough was collected.

Percent of cells bound to beads in the capture column was calculated using the calculation:

$$\text{Percent bound} = \frac{\text{Reference count} - \text{Flowthrough count}}{\text{Reference count}}$$

III. Dead Cell Capture Analysis

A 10 mL dead cell reference sample was created by heating 10 mL of live cells in capture buffer in a tube to 72 °C for 5 minutes, such as in a water bath on hotplate. The live cell capture analysis procedure was repeated using the 10 mL dead cell reference sample.

The live cell analysis was compared to the dead cell analysis to confirm only live cell were captured.

IV. Confirmation

For optical cell counting using a Neubauer Hemocytometer and the 40× lens on an optical microscope, an aliquot of washed cells was diluted sufficiently (for example, 15-fold) and a 5 μL aliquot placed under a coverslip on the Hemocytometer to result in approximately 15 cells on average counted per square. This count established a reference count for a known (e.g., 15-fold) dilution of prepared cells.

V. Run and Data

All studies followed the standard process to measure cell capture efficiency as follows:

1. Dilute *Listeria* cell culture to achieve a cell count of approximately 14-18 counts per square using hemocytometer.
2. Take a 5 μL aliquot of a 10 mL reference sample and count cells.
3. Flow reference sample through capture column and collect entire flow through.
4. Count cells in flow through.
5. To determine percentage of dead cells, combine an aliquot of reference suspension and an equal volume of trypan blue. Count number of all cells and number of blue (dead) cells.

Capture buffer using diluted and reference counts averaged 14.8. No cells took up trypan blue which is consistent with all live cells from a fresh culture. The live cell suspension was flowed through the capture column and flow-through counts averaged 3.3 cells per square, equating to a capture efficiency of 78%.

The following day, *Listeria* cells from the same culture were heated to approximately 72 °C for at least 2 minutes. Cells were confirmed dead with trypan blue dye (all cells were blue and no individual counts were recorded). The dead cell suspension flowed through the capture column and flow-through counts averaged 17.2, demonstrating that no dead cells bound.

| | | Counts | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|---|
| 1 | Live cell analysis | Reference | 16 | 12 | 15 | 16 | 16 | 14 | | | | | | | | | |
| | Dec. 24, 2018 | Flow-thru | 6 | 2 | 2 | 5 | 1 | 4 | 4 | 4 | 3 | 2 | 1 | 5 | | | |
| 2 | Dead cell analysis | Reference | 16 | 18 | 17 | 17 | 18 | 17 | | | | | | | | | |
| | Dec. 26, 2018 | Flow-thru | 16 | 18 | 17 | 17 | 18 | 16 | | | | | | | | | |

| | | Counts | 16 | 17 | 18 | Average | % bound/dead | Results |
|---|---|---|---|---|---|---|---|---|
| 1 | Live cell analysis | Reference | | | | 14.8 | 78% bound | 78% Live cells |
| | Dec. 24, 2018 | Flow-thru | | | | 3.3 | | captured |
| 2 | Dead cell analysis | Reference | | | | 17.2 | 1% bound | 1% (dead cells |
| | Dec. 26, 2018 | Flow-thru | | | | 17.0 | | captured) |

The data show that live *Listeria* cells bound at high efficiency (78%), while heat-treated (dead) cells did not bind at all. This demonstrates the disclosed cell capture system/process does not bind dead *Listeria* cells.

Example 4

Cultured *Listeria* Cells Spiked into Samples are Processed by Disclosed System and Analyzed Using RT-PCR I. Setup The device shown in FIG. 8 includes a first of a sample input chamber 8500, heat exchanger 8501, pre-filter 8402, cell capture column 8403, lysis filter 8404, waste collection 8502 and PCR sample collection tube 8503. The device is inserted into the instrument which comprises a number of further fluidic components. Collectively, a fluidic circuit is formed using biocompatible system tubing.

The sample input chamber, heat exchanger, pre-filter, cell capture column, lysis filter, waste collection and PCR sample collection tube are all connected to peristaltic pump using biocompatible peristaltic pump tubing connected to biocompatible system tubing, while the output of the lysis filter is connected to a syringe pump using biocompatible system tubing, and the system is placed in an environmental chamber at approximately 10 °C to 12 °C.

II. Condition the System

The system is conditioned by flowing approximately 15 mL of capture buffer through the prefilter and capture column at 10 ml/min using peristaltic pump and discarding the flow-through buffer then by flowing approximately 15 mL of capture buffer through the capture column at 30 ml/min.

III. Live Cell Capture and Release

A live cell spiked sample of 10 to 100 mL is created using cells diluted in capture buffer or an environmental sample, and a 5 μL reference count aliquot is taken from the sample to determine approximate cell concentration. A second 5 μL aliquot is taken for trypan blue testing to confirm all cells are live. An air gap is introduced after the last sample buffer wash to prevent dilution and mixing of release buffer with capture buffer. The 10 to 100 mL sample is flowed through capture column at flow rate of approximately 15 mL/min, and the flow-through is discarded. Immediately following the sample, approximately 5 mL of capture buffer is flowed through the prefilter and capture column and the flow-through is discarded. A second volume of approximately 5 mL sample buffer is flowed through the capture column and flow through is discarded. Release buffer is flowed through the system, bypassing the prefilter, and passing through the capture column and lysis filter and flow-through is discarded. Lysis filter is flowed through the lysis filter and flow-through is discarded. Air is flowed through the lysis filter to clear excess liquid, which is discarded, from the system tubing.

A 50 μL aliquot of lysis buffer is back-flowed through the lysis filter and collected in a PCR tube containing primers, probes, and enzymes such as used for PCR amplification and *Listeria* detection.

The back-flowed sample and PCR reagents undergo ultrasonic bead beating in the PCR tube to extract nucleic acids such as with using Zirconia beads and a sonic transducer for two minutes to generate a PCR. The PCR tube with extracted sample is placed in a PCR instrument for analysis.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method for detecting, quantitating, or monitoring pathogens, the method comprising:

capturing one or more live pathogens from a contaminating matrix within a sample by aptamer-based capture or antibody-based capture, wherein the step of capturing includes (a) reducing sodium concentration to less than 100 mM in pathogen capturing conditions and (b) reducing temperature to less than 20 degrees Celsius in pathogen capturing conditions; and releasing the one or more captured live pathogens from aptamers or antibodies, thereby allowing the one or more live pathogens to be detected, quantitated, or monitored without requiring cell culture.

2. The method of claim 1, wherein the one or more live pathogens is one or more disease producing organism, wherein the one or more disease producing organisms are bacteria, fungi, protozoa, or worms.

3. The method of claim 1, wherein the one or more live pathogens is one or more pathogens in a sample from food, water, environment, soil, plant, animal, insect, or human.

4. The method of claim 1, wherein the step of capturing one or more live pathogens comprises applying the sample to a pathogen-isolation column containing multiple beads of one or more sizes.

5. The method of claim 4, wherein the pathogen-isolation column comprises a pipe having a constant cross-sectional area along a longitudinal axis of the pipe.

6. The method of claim 4, wherein the pathogen-isolation column comprises a pipe having a varying cross-sectional area along a longitudinal axis of the pipe.

7. The method of claim 4, wherein a cross-section of the pathogen-isolation column is of a uniform shape, and wherein the uniform shape is one of a circle, oval, or polygon.

8. The method of claim 4, wherein a cross-section of the pathogen-isolation column is of a non-uniform shape.

9. The method of claim 1, further comprising providing magnesium at a concentration sufficient to increase aptamer melting temperatures to result in a stable secondary structure formation.

10. The method of claim 9, wherein the concentration of magnesium is greater than 0.1 mM.

11. The method of claim 4, wherein a bead surface of each of the multiple beads comprises a material modified for aptamer or antibody attachment.

12. The method of claim 1, wherein the step of capturing one or more live pathogens further comprises applying the sample to a pre-filter container containing beads of same size or smaller than a pathogen-isolation column prior to the pathogen-isolation column containing multiple beads of one or more sizes.

13. The method of claim 12, wherein the beads of the pre-filter container have non-fouling surface properties.

14. The method of claim 12, wherein the step of capturing one or more live pathogens from aptamers or antibodies, comprises:

optional conditioning of the pre-filter container and capture column by flowing liquid through the pre-filter container and capture column.

15. The method of claim 1, wherein the sample is a pathogen sample.

16. The method of claim 1, further comprising washing the one or more live captured pathogens prior to releasing the live captured one or more pathogens to remove substances not specifically bound.

17. The method of claim 16, wherein the substances not specifically bound comprise nontargeted organisms and nucleic acid amplification inhibitors.

18. The method of claim 1, wherein the step of releasing the one or more live captured pathogens from aptamers or antibodies comprises washing the captured one or more live pathogens with a release buffer.

19. The method of claim 18, wherein the step of releasing the one or more captured live pathogens from aptamers or antibodies is performed by using a flow rate equal to or higher than the flow rate used to capture the one or more pathogens.

20. The method of claim 19, wherein a flow rate for releasing the one or more captured live pathogens from aptamers or antibodies is at least twice higher than a flow rate for capturing the one or more live pathogens.

21. The method of claim 1, wherein the step of releasing the one or more live captured pathogens from aptamers or antibodies comprises an air gap prior to washing the captured one or more live pathogens with a release buffer.

22. The method of claim 21, wherein the released live pathogens are collected in liquid in a vented bubble trap acting as a reservoir and acting to remove air prior to the one or more live pathogens in liquid are flowed through a filter to collect the released one or more pathogens.

23. The method of claim 22, wherein the vented bubble trap comprises at least one inlet port, at least one outlet port, and a vent to air.

24. The method of claim 23, wherein the vent comprises one or more sensors that permit feedback control of volume of liquid pumped into the vented bubble trap.

25. The method of claim 24, wherein the one or more sensors comprise one or more liquid level sensors capable of detecting liquid level or one or more bubble sensors capable of detecting bubbles in the liquid.

26. The method of claim 1, wherein the method is aptamer-based used to specifically sequester pathogens away from the contaminating matrix.

27. The method of claim 26, wherein each of the aptamers contains DNA, RNA, PNA, peptide or other natural or synthetic molecules.

28. The method of claim 1, further comprising detecting, quantitating, or monitoring pathogens by performing a nucleic acid detection following the step of releasing the one or more captured live pathogens.

29. The method of claim 28, wherein the nucleic acid detection comprises detecting DNA or RNA.

30. The method of claim 28, wherein the nucleic acid detection comprises performing polymerase chain reaction, isothermal amplification, hybridization detection, or sequencing.

31. The method of claim 1, wherein the step of capturing or releasing one-or-more-steps is performed by automation.

32. The method of claim 1, further comprising sanitizing after the one or more live pathogens are detected, quantitated, or monitored.

33. The method of claim 32, wherein the step of sanitizing comprises employing a sanitation system comprising a cartridge and a sanitation solution.

34. The method of claim 1, further comprising applying a sample temperature by one or more cooling or heating elements to heat or cool the sample prior to pathogen capture.

35. A method for detecting, quantitating or monitoring pathogens, the method comprising:

capturing one or more foodborne pathogens from a contaminating matrix within a sample by aptamer-based pathogen capture or antibody/antigen pathogen capture, wherein the step of capturing includes (a) reducing sodium concentration to less than 100 mM in pathogen capturing conditions, (b) reducing temperature to less than 20 degrees Celsius in pathogen capturing conditions, and (c) providing magnesium at a concentration greater than 0.1 mM and sufficient to increase aptamer melting temperatures to result in a stable secondary structure formation; and releasing the one or more captured foodborne pathogens from aptamers or antibodies, thereby allowing the one or more foodborne pathogens to be detected, quantitated, or monitored without requiring cell culture.

36. A method for capturing live pathogens from a contaminating sample matrix by aptamer-based pathogen capture, comprising:

reducing sodium concentration to less than 100 mM in pathogen capturing conditions;

reducing temperature to less than 20 degrees Celsius in pathogen capturing conditions; and providing magnesium at a concentration greater than 0.1 mM and sufficient to increase aptamer melting temperatures to result in a stable secondary structure formation.

37. The method of claim 36, further comprising applying a sample temperature by one or more cooling or heating elements to transfer the sample temperature to the sample prior to pathogen capture.

38. A method for capturing live pathogens from a contaminating sample matrix by aptamer-based pathogen capture, comprising:

reducing sodium concentration to less than 70 mM in pathogen capturing conditions;

reducing temperature to less than 20 degrees Celsius in pathogen capturing conditions; and providing magnesium at a concentration greater than 0.25 mM and sufficient to increase aptamer melting temperatures to result in desired secondary structure formation.

39. The method of claim 38, further comprising applying a sample temperature by one or more cooling or heating elements to transfer the sample temperature to the sample prior to pathogen capture.

40. A method for detecting, quantitating, or monitoring infectious particles, the method comprising:

capturing one or more infectious particles from a contaminating matrix within a sample by aptamer-based capture or antibody/antigen capture, wherein the step of capturing includes (a) reducing sodium concentration to less than 100 mM in pathogen capturing conditions, (b) reducing temperature to less than 20 degrees Celsius in pathogen capturing conditions, and (c) providing magnesium at a concentration greater than 0.1 mM and sufficient to increase aptamer melting temperatures to result in a stable secondary structure formation; and releasing the one or more captured infectious particles from aptamers or antibodies, thereby allowing the one or more infectious particles to be detected, quantitated, or monitored without requiring cell culture.

41. The method of claim 40, wherein the one or more infectious particles is one of bacteria, viruses, fungi, protozoa, worms, proteins, peptides and allergens.

42. The method of claim 40, wherein the step of capturing one or more infectious particles comprises applying the sample to an isolation column containing multiple beads of one or more sizes.

43. The method of claim 42, wherein a bead surface of each of the multiple beads comprises a material modified for aptamer or antibody attachment.

44. The method of claim 43, wherein the step of capturing one or more infectious particles further comprises applying the sample to a pre-filter container containing beads of same size or smaller than the isolation column prior to the isolation column containing multiple beads of one or more sizes.

45. The method of claim 44, wherein the beads of the pre-filter container have non-fouling surface properties.

46. The method of claim 45, further comprising washing the one or more captured infectious particles prior to the step of releasing the one or more captured infectious particles.

47. The method of claim 46, wherein the one or more released captured infectious particles from aptamers or antibodies are concentrated prior to a detection.

48. The method of claim 47, wherein the aptamer contains DNA, RNA, PNA, peptides or other natural or synthetic molecules.

49. The method of claim 48, further comprising nucleic acid extraction prior to the detection.

50. The method of claim 49, wherein the detection includes a nucleic acid detection comprising detecting DNA or RNA.

51. The method of claim 50, wherein the nucleic acid detection comprises performing polymerase chain reaction, isothermal amplification, hybridization detection, or sequencing.

* * * * *